(12) United States Patent
Shirai et al.

(10) Patent No.: US 9,977,105 B2
(45) Date of Patent: May 22, 2018

(54) MAGNETIC RESONANCE IMAGING DEVICE AND WATER-FAT SEPARATION METHOD

(71) Applicant: Hitachi, Ltd., Tokyo (JP)

(72) Inventors: Toru Shirai, Tokyo (JP); Yo Taniguchi, Tokyo (JP); Hisaaki Ochi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 347 days.

(21) Appl. No.: 14/904,202

(22) PCT Filed: Aug. 7, 2013

(86) PCT No.: PCT/JP2013/071390
§ 371 (c)(1),
(2) Date: Jan. 11, 2016

(87) PCT Pub. No.: WO2015/019449
PCT Pub. Date: Feb. 12, 2015

(65) Prior Publication Data
US 2016/0161580 A1    Jun. 9, 2016

(51) Int. Cl.
*G01V 3/00* (2006.01)
*G01R 33/48* (2006.01)
(Continued)

(52) U.S. Cl.
CPC ............ *G01R 33/4828* (2013.01); *A61B 5/00* (2013.01); *A61B 5/055* (2013.01);
(Continued)

(58) Field of Classification Search
USPC ........................................................ 324/322
See application file for complete search history.

(56) References Cited

U.S. PATENT DOCUMENTS 6,459,922 B1    10/2002  Zhang
6,995,560 B2 *  2/2006   Duerk ................ G01R 33/4828
                                                          324/306

(Continued)

FOREIGN PATENT DOCUMENTS

JP    2000-300539 A    10/2000
WO    2011/108314 A1    9/2011

OTHER PUBLICATIONS

W. Thomas Dixon, Ph.D. "Simple Proton Spectroscopic Imaging" Radiology, Oct. 1984, pp. 189-194, vol. 153.
(Continued)

*Primary Examiner* — Rodney Fuller
(74) *Attorney, Agent, or Firm* — Mattingly & Malur, PC

(57) ABSTRACT

Restriction on echo intervals is to be reduced in the Dixon's method without sacrificing separation performance and image quality. An image is reconstructed from echo signals measured at three or more different echo times. First and second peak frequency distributions in which aliasing (folding) due to echo time intervals is removed are calculated from the obtained images, and the first and second peak frequency distributions are used to obtain an offset frequency distribution. Note that these first peak frequency distribution and second peak frequency distribution are a distribution of peak frequencies obtained on the assumption that all of the pixels are the first substance and a distribution of peak frequencies obtained on the assumption that all of the pixels are the second substance, respectively. The offset frequency distribution and the obtained images are used to separate an image of the first substance from an image of the second substance.

15 Claims, 11 Drawing Sheets

(51) Int. Cl.
| | |
|---|---|
| A61B 5/055 | (2006.01) |
| A61B 5/00 | (2006.01) |
| G01R 33/34 | (2006.01) |
| G01R 33/54 | (2006.01) |
| G01R 33/56 | (2006.01) |
| G01R 33/38 | (2006.01) |
| G01R 33/485 | (2006.01) |

(52) U.S. Cl.
CPC ..... *G01R 33/34053* (2013.01); *G01R 33/543* (2013.01); *G01R 33/5607* (2013.01); *G01R 33/3806* (2013.01); *G01R 33/485* (2013.01); *G01R 33/5608* (2013.01)

(56) References Cited

U.S. PATENT DOCUMENTS

| | | | | |
|---|---|---|---|---|
| 2004/0032977 | A1* | 2/2004 | Blezek | G01R 33/4828 382/128 |
| 2012/0301007 | A1 | 11/2012 | Shirai et al. | |
| 2014/0002080 | A1* | 1/2014 | Den Harder | G01R 33/445 324/309 |
| 2015/0123658 | A1* | 5/2015 | Zhong | G01R 33/4828 324/309 |
| 2016/0082133 | A1* | 3/2016 | Gilad | A61K 49/12 424/9.35 |

OTHER PUBLICATIONS

Jingfei Ma "Breath-Hold Water and Fat Imaging Using a Dual-Echo Two-Point Dixon Technique With an Efficient and Robust Phase-Correction Algorithm" Magnetic Resonance in Medicine, 2004, pp. 415-419, vol. 52.
Scott B. Reeder, et al. "Multicoil Dixon Chemical Species Separation With an Iterative Least-Squares Estimation Method" Magnetic Resonance in Medicine, 2004, pp. 35-45, vol. 51.
Huanzhou Yu, et al. "Multiecho Reconstruction for Simultaneous Water-Fat Decomposition and T2 Estimation" Journal of Magnetic Resonance Imaging, 2007, pp. 1153-1161, vol. 26.
International Search Report of PCT/JP2013/071390.
International Preliminary Report on Patentability received in corresponding International Application No. PCT/JP2013/071390 dated Feb. 18, 2016.
Berglund, J. et al., "Closed-Form Solution for the Three-Point Dixon Method with Advanced Spectrum Modeling", Proc. Int. Soc. Magnetic Resonance Medicine, Jul. 13, 2011, p. 751.
Berglund, J. et al., "Three-Point Dixon Method Enables Whole-body Water and Fat Imaging of Obese Subjects", Magnetic Resonance in Medicine, May 21, 2010, pp. 1659-1668, vol. 63 Issue 6.
Yu, H. et al., "Multiecho Water-Fat Separation and Simultaneous R2 Estimation with Multifrequency Fat Spectrum Modeling", Magnetic Resonance in Medicine, Oct. 27, 2008, pp. 1122-1134, vol. 60 Issue 5.

* cited by examiner

MAGNETIC RESONANCE IMAGING DEVICE AND WATER-FAT SEPARATION METHOD

TECHNICAL FIELD

The present invention relates to a magnetic resonance imaging (hereinafter referred to as MRI) technology, and more particularly to a technology for separating signals from unnecessary substances to obtain an image with reduced signals of such substances.

BACKGROUND ART

The MRI converts spatial distribution of information on relaxation of proton density and nuclear magnetic resonance signals (hereinafter referred to as NMR signals) into an image so as to obtain form information or functional information of the head, abdomen, limbs, etc. of a human. The nuclides to be imaged with the MRI which are widely used in clinical practice at present are hydrogen nuclei (protons) that are main components of a subject.

For measuring a human body, examples of main substances from which NMR signals from protons can be detected with the MRI include water and fat. For converting NMR signals from water protons (hereinafter referred to as water signals) into an image, the image contrast of NMR signals from fat proton (hereinafter referred to as fat signals) is lowered. In clinical practice, a method for suppressing in vivo fat signals is therefore proposed.

An example of the technique for suppressing signals from unnecessary substances other than the substances to be imaged is the Dixon's method in which the difference in resonance frequency between substances are used (refer to NPL 1, for example). The Dixon's method separates signals of respective substances with use of the resonance frequency difference so as to obtain an image in which signals of unnecessary substances are suppressed. The resonance frequency difference is called a chemical shift, and the resonance frequency difference between water and fat is 3.5 ppm, for example. The resonance frequency difference that is a chemical shift is proportional to magnetic field strength, and is approximately 448 Hz when the magnetic field strength is 3 teslas.

The Dixon's method obtains an image from each of a plurality of NMR signals (hereinafter referred to as echo signals) that are different in the time (hereinafter referred to as the echo time) from excitation of hydrogen nuclear spins until acquisition of the echo signal. There are methods called the two-point Dixon (2PD) method and the three-point Dixon (3PD) method depending on the number of echo times to be measured.

In the 2PD method, images obtained from echo signals measured at two different echo times are used for estimation of an offset frequency distribution. The offset frequency distribution is a distribution of offset amounts of resonance frequencies varying spatially owing to inhomogeneous magnetostatic field. This is then used for calculation of an image (hereinafter referred to as a water image) in which the strengths of water signals are pixel values and an image (hereinafter referred to as a fat image) in which the strengths of fat signals are pixel values, for example (refer to NPL 2, for example). In the 3PD method, images obtained from echo signals measured at three different echo times are used for calculation of a water image, a fat image, and an offset frequency distribution (refer to NPL 3, for example).

Furthermore, there is also a technique called the Multi Point Dixon (MPD) method in which images at four or more echo times are measured, and a water image and a fat image, an offset frequency distribution, and an apparent transverse magnetization relaxation rate ($R_{2*}$) distribution are calculated (refer to NPL 4, for example). The MPD method is used in a super-high magnetic field MRI of 3 teslas or higher with greatly inhomogeneous magnetostatic field and transmission magnetic field and in a fat suppressing method for an abdomen, a cervical spine region, etc. The MPD method is also used for quantification of fat signals, evaluation of hepatic steatosis diseases through identification of iron deposits in a liver, etc.

CITATION LIST

Non-Patent Literature

NPL 1: Thomas Dixon et al. "Simple Proton Spectroscopic Imaging," Radiology, vol. 153, 1984, pp. 189-194

NPL 2: Jingfei Ma "Breath-Hold Water and Fat Imaging Using a Dual-Echo Two-Point Dixon Technique With an Efficient and Robust Phase-Correction Algorithm," Magnetic Resonance in Medicine, vol. 52, 2004, pp. 415-419

NPL 3: Scott B. Reeder et al. "Multicoil Dixon Chemical Species Separation With an Iterative Least-Squares Estimation Method," Magnetic Resonance in Medicine, vol. 51, 2004, pp. 35-450

NPL 4: Huanzhou Yu et al. "Multiecho Reconstruction for SimultaneousWater-Fat Decomposition an$\Delta t2^*$ Estimation," Journal of Magnetic Resonance Imaging, vol. 26, 2007, pp. 1153-1161

SUMMARY OF INVENTION

Technical Problem

In the 2PD method, it is necessary to set echo times with which the offset frequency distribution can be easily calculated, which allows little flexibility in setting the echo times. In the Dixon's methods such as the 3PD method and the MPD method in which measurements are performed a three or more different echo times, intervals between the echo times (hereinafter referred to as echo intervals) need to be set to satisfy a sampling theorem in order to prevent aliasing of fat signals. Herein, the resonance frequency difference between water and fat is defined as a Nyquist frequency. If images are measured at echo intervals that do not satisfy the sampling theorem, aliasing of fat signals is caused in the frequency direction. If a conventional separation process is performed in this state, water and fat may be replaced with each other in calculation or separation accuracy may be lowered.

If the echo intervals are set to satisfy the sampling theorem in order to prevent the above, restriction on the length of time for signal acquisition (AD) is caused and it is difficult to increase spatial resolution and to improve the signal to noise ratio (SNR).

The present invention has been made in view of the aforementioned circumstances, and an object thereof is to provide a technology for reducing restriction on echo intervals in the Dixon's method without sacrificing separation performance and image quality.

Solution to Problem

The present invention reconstructs an image from each of echo signals measured at three or more different echo times.

A first peak frequency distribution and a second peak frequency distribution in which aliasing (folding) in the frequency direction due to echo time intervals is removed are calculated from the obtained images, and the first peak frequency distribution and the second peak frequency distribution are used to obtain an offset frequency distribution. Note that these first peak frequency distribution and second peak frequency distribution are a distribution of peak frequencies obtained on the assumption that all of the pixels are the first substance and a distribution of peak frequencies obtained on the assumption that all of the pixels are the second substance, respectively. The offset frequency distribution and the obtained images are used to separate an image of the first substance from an image of the second substance.

Advantageous Effects of Invention

According to the present invention, restriction on echo intervals can be reduced in the Dixon's method without sacrificing separation performance and image quality.

DESCRIPTION OF EMBODIMENTS

First Embodiment

Figure 1:
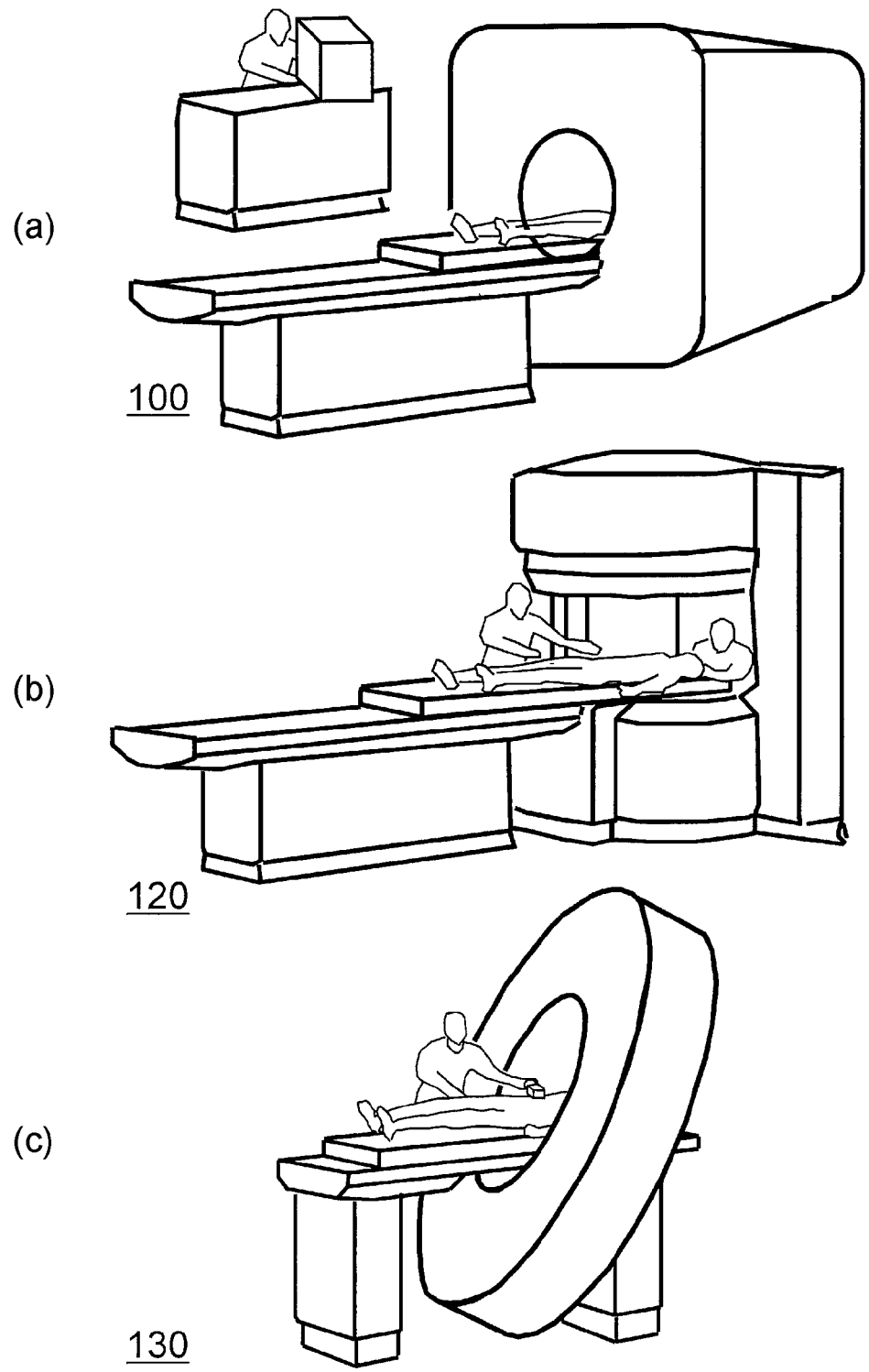
FIG. 1(a) is an external view of a horizontal magnetic field MRI apparatus of MRI apparatuses according to an embodiment of the present invention.
FIG. 1(b) is an external view of a vertical magnetic field MRI apparatus of the MRI apparatuses according to the embodiment of the present invention.
FIG. 1(c) is an external view of a MRI apparatus with obliquely-tilted tunnel-shaped magnet of the MRI apparatuses according to the embodiment of the present invention.

A first embodiment of the present invention will be described below. Hereinafter, in all of the drawings for describing the embodiments, components having the same functions will be designated by the same reference numerals unless otherwise stated and redundant description will not be repeated.

<External Appearance of MRI Apparatus>

First, magnetic resonance imaging apparatuses (MRI apparatuses) according to the present embodiment will be described. FIGS. 1(a) to 1(c) are external views of the MRI apparatuses according to the present embodiment. FIG. 1(a) is a horizontal magnetic field MRI apparatus 100 with a tunnel-shaped magnet that generates a magnetostatic field with a solenoidal coil. FIG. 1(b) is a vertical magnetic field MRI apparatus 120 having a hamburger shape (open shape) in which separate magnets are vertically arranged so that spaciousness is increased. FIG. 1(c) is a MRI apparatus 130 with the same tunnel-shaped magnet as that in FIG. 1(a), but the magnet is reduced in depth and tilted obliquely so that spaciousness is increased.

In the present embodiment, any of the MRI apparatuses having these external appearances may be used. Note that these are only examples, and the MRI apparatuses of the present embodiment are not limited to these shapes. In the present embodiment, various known MRI apparatuses can be used regardless of the shapes and the types of the apparatuses. Hereinafter, the MRI apparatuses will be represented by the MRI apparatus 100 unless the MRI apparatuses particularly need to be distinguished.

<Functional Configuration of MRI Apparatus>

Figure 2:
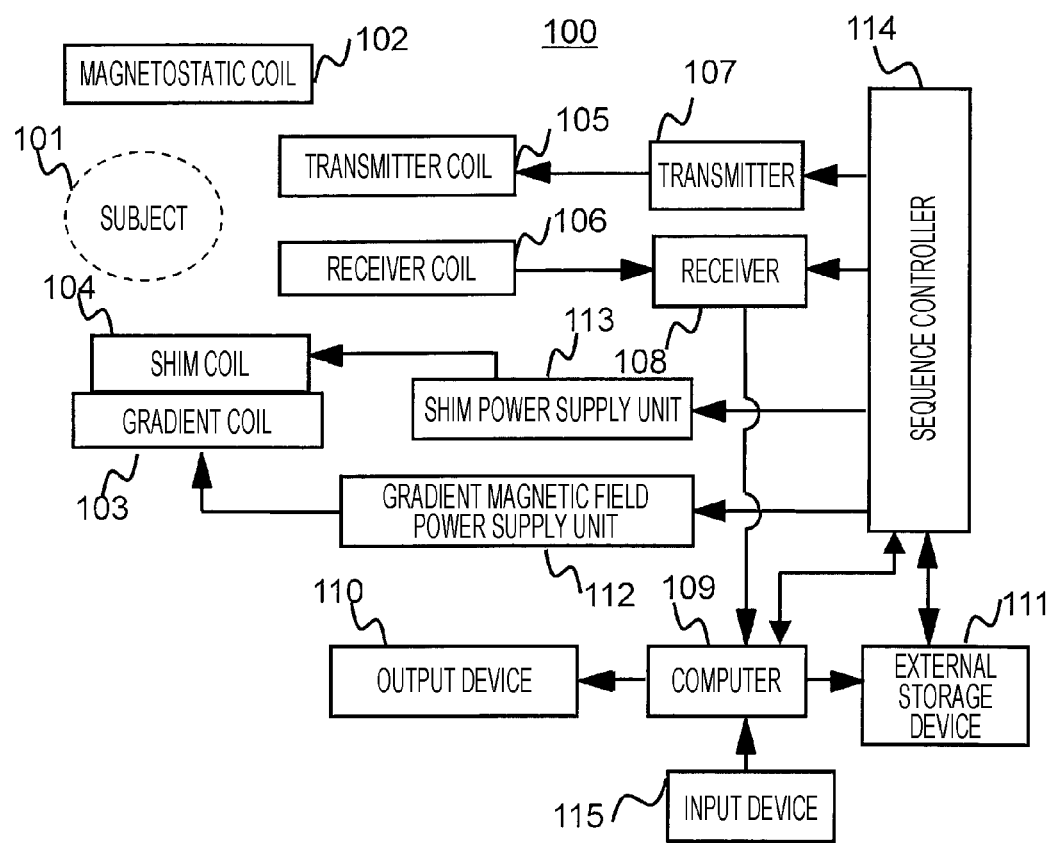
FIG. 2 is a functional configuration diagram of a MRI apparatus according to a first embodiment.

FIG. 2 is a functional configuration diagram of the MRI apparatus 100 according to the present embodiment. As illustrated in FIG. 2, the MRI apparatus 100 of the present embodiment includes a magnetostatic field generation part such as a magnetostatic coil 102 for generating a magnetostatic field in a space in which a subject 101 is placed, a shim coil 104 and a shim power supply unit 113 for controlling magnetostatic field distribution, a transmitting unit including a radio frequency transmitter coil 105 (hereinafter simply referred to as a transmitter coil) an a transmitter 107 for transmitting radio frequency magnetic field pulses to a region to be measured of the subject 101, a receiving unit including a radio frequency receiver coil 106 (hereinafter simply referred to as a receiver coil) and a receiver 108 for receiving nuclear magnetic resonance signals generated from the subject 101, a gradient magnetic field application part including a gradient coil 103 and a gradient magnetic field power supply unit 112 for applying a gradient magnetic field to each of an x direction, a y direction, and a z direction so as to add positional information to the nuclear magnetic resonance signals generated from the subject 101, a computer 109, and a sequence controller 114.

For the magnetostatic coil 102, a coil having any of various shapes depending on the structure of the MRI apparatus 100, 120, or 130 illustrated in FIG. 1(a), FIG. 1(b), or FIG. 1(c), respectively, is used. The gradient coil 103 and the shim coil 104 are driven by the gradient magnetic field power supply unit 112 and the shim power supply unit 113, respectively. While an example in which the transmitter coil 105 and the receiver coil 106 are separately provided is described in the present embodiment, a single coil having the functions of both the transmitter coil 105 and the receiver coil 106 may alternatively be used. The radio frequency magnetic field irradiated by the transmitter coil 105 is generated by the transmitter 107. The nuclear magnetic resonance signals detected by the receiver coil 106 are transmitted to the computer 109 via the receiver 108.

The sequence controller 114 controls operations of the gradient magnetic field power supply unit 112 that is a power supply for driving the gradient coil 103, the shim power supply unit 113 that is a power supply for driving the shim coil 104, the transmitter 107, and the receiver 108, controls reception timings of application of the gradient magnetic field and the radio frequency magnetic field and reception of the nuclear magnetic resonance signals, and performs measurements. A time chart of the control is called an imaging sequence, set in advance according to the measurements, and stored in a storage device or the like included in the computer 109, which will be describe later.

The computer 109 controls operations of the transmitting unit, the receiving unit, and the gradient magnetic field application part and performs computation on received echo signals to obtain an image of a predetermined imaged region. Functions implemented by the computer 109 will be described later. The computer 109 is an information processing device including a CPU, a memory, a storage device, etc., and a display device 110, an external storage device 111, an input device 115, etc. are connected to the computer 109.

The display device 110 is an interface for displaying results, etc. obtained through the computation for the operator. The input device 115 is an interface for the operator to input conditions, parameters, etc. necessary for the measurements and computation carried out in the present embodiment. In the present embodiment, the user can input measurement parameters such as the number of echoes to be measured, a reference echo time, and echo intervals through the input device 115. The external storage device 111 together with the storage device holds data used for various computations carried out by the computer 109, data obtained through the computations, input conditions, input conditions, parameters, etc.

<Functions Implemented by Computer>

Functions implemented by the computer 109 of the present embodiment will be described. The computer 109 of the present embodiment controls the respective components of the MRI apparatus 100 as described above, and performs an imaging process of converting a predetermined region to be imaged (space to be imaged) into an image. In this process, at the region to be imaged, it is assumed that signals from protons in substances other than a first substance to be imaged and a second substance that is unnecessary can be ignored. On this assumption, signals from protons in the first substance and signals from protons in the second substance are separated from each other, so that an image in which signal strengths of the first substance are pixel values and in which the signals from the second substance are suppressed is obtained.

Figure 3:
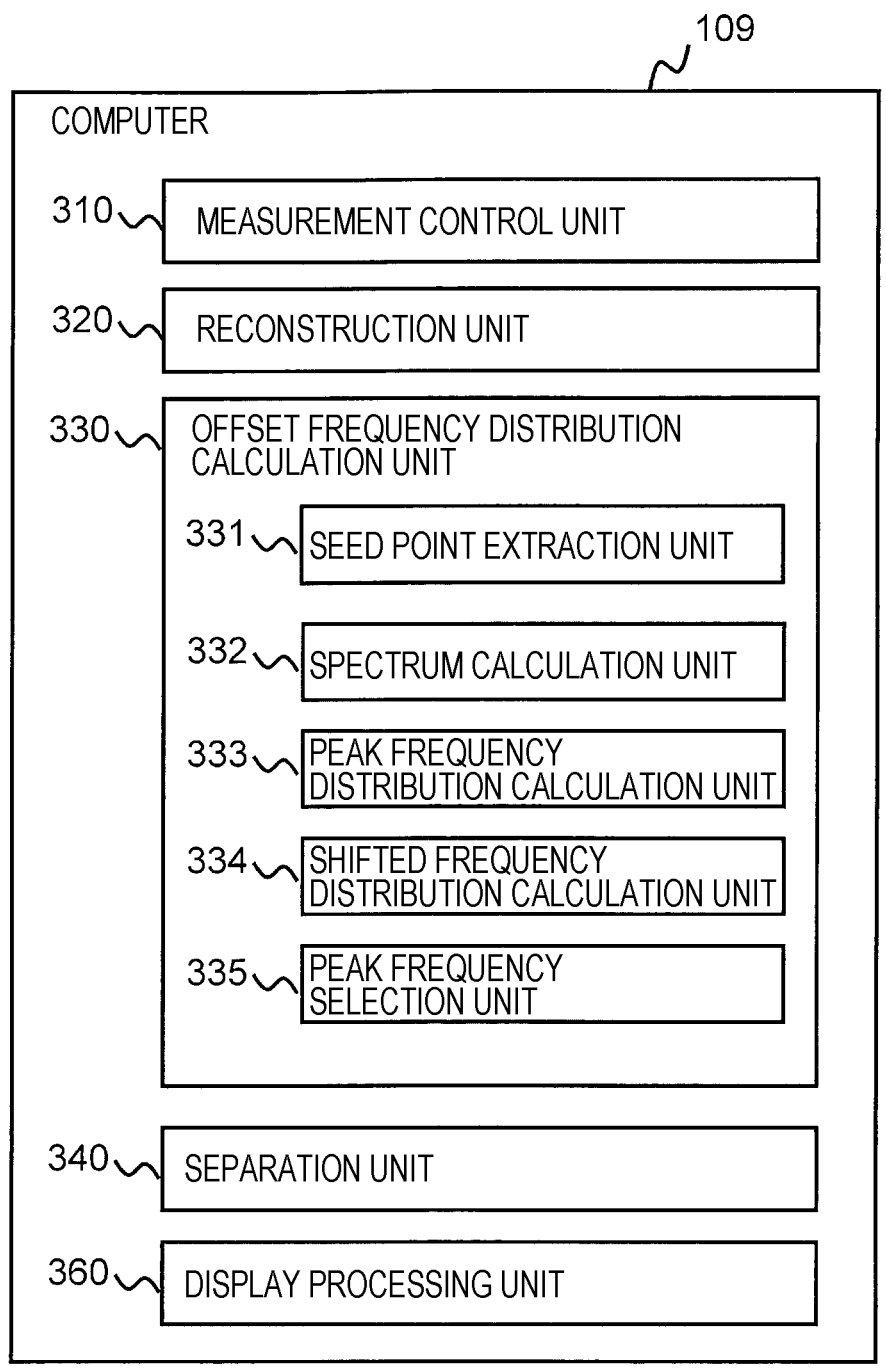
FIG. 3 is a functional block diagram of a computer according to the first embodiment.

Hereinafter, in the present embodiment, an example in which the substances to be separated are water and fat and in which the first substance water and the second substance is fat will be described. FIG. 3 is a functional block diagram of the computer 109 according to the present embodiment. The computer 109 of the present embodiment includes a measurement control unit 310, a reconstruction unit 320, an offset frequency distribution calculation unit 330, a separation unit 340, and a display processing unit 360.

The measurement control unit 310 acquires an echo signal at each of three or more different echo times from the region to be measured according to a predetermined measurement sequence. The measurement sequence is generated on the basis of the parameters input by the user through the input device 115 and a pulse sequence stored in the storage device or the like in advance. The measurement control unit 310 gives instructions to the sequence controller 114 according to the generated measurement sequence to carryout measurement of the imaged region.

The reconstruction unit 320 reconstructs a raw image at each echo time of the imaged region from the echo signals acquired by the measurement control unit 310. The raw image is obtained by placing the acquired echo signal in a k space and applying Fourier transform thereon at each echo time. Hereinafter, in the present specification, the number of echoes to be measured is N (N is an integer of 3 or larger) and a raw image at the n-th (n=1, 2, 3, . . . , N) echo time $t_n$ will be represented by $I_n$. Furthermore, each raw image $I_n$ and a water image and a fat image that are finally obtained have the same pixel size.

The offset frequency distribution calculation unit 330 calculates offset frequency distribution of the imaged region from the raw images $I_n$ at the respective echo times. In the present embodiment, raw images $I_n$ at N different echo times are used for calculation of one offset frequency distribution. The offset frequency distribution is a distribution of offset components (offset frequencies) of resonance frequencies of respective pixels which vary owing to an inhomogeneous magnetostatic field.

The separation unit 340 separates signals of the first substance (water signals) and signals of the second substance (fat signals) by using the raw images $I_n$ at the respective echo times and the offset frequency distribution to obtain an image of the first substance (water image) and an image of the second substance (fat substance) of the imaged region.

The display processing unit 360 displays the water image and the fat image resulting from the separation on the display device 110. The display processing unit 360 may also display information making the water image and the fat image distinguishable from each other in displaying the water image and the fat image on the display device 110. The information making the images distinguishable may be captions such as "water image" and "fat image", for example. Furthermore, an image calculated during the imaging process such as the offset frequency distribution may also be displayed on the display device 110 where necessary.

Note that the functions implemented by the computer 109 are implemented by loading programs held in the storage device into the memory and executing the programs by the CPU. Furthermore, at least one of the functions implemented by the computer 109 may be implemented by an information processing device independent of the MRI apparatus 100 and capable of transmitting and receiving data to/from the MRI apparatus 100.

<Processing Flow of Imaging Process>

Figure 4:
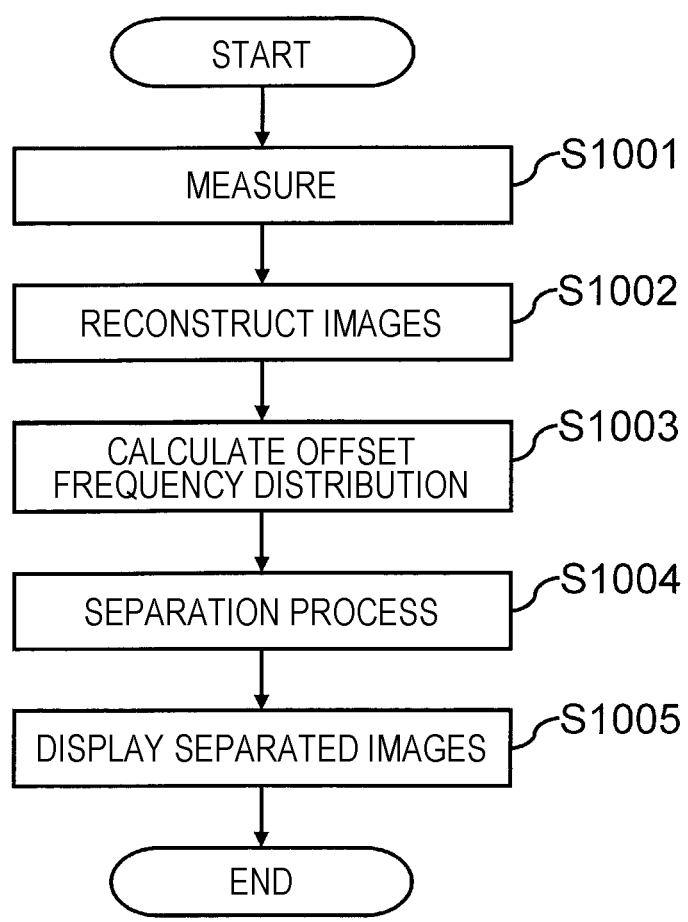
FIG. 4 is a flowchart of an imaging process according to the first embodiment.

Hereinafter, a processing flow of the imaging process performed by the functions of the computer 109 of the present embodiment will be briefly described. FIG. 4 is a flowchart for illustrating a processing flow of the imaging process of the present embodiment.

In the present embodiment, raw images $I_n$ at N echo times $t_n$ are obtained, and the N raw images $I_n$ are used to calculate an offset frequency distribution due to inhomogeneous magnetostatic field. The offset frequency distribution and the raw images $I_n$ are then used to obtain water images and fat images resulting from separation of water and fat.

First, the measurement control unit 310 gives instructions to the sequence controller 114 according to the predetermined measurement sequence to measure echo signals at the N respective echo times $t_n$ (step S1001).

The reconstruction unit 320 places the echo signal at each echo time in the k space and applies Fourier transform thereto to reconstruct each of the N raw images $I_n$ at the echo times $t_n$ (step S1002).

The offset frequency distribution calculation unit 330 calculates one offset frequency distribution from the N obtained raw images $I_n$ (step S1003).

Subsequently, the separation unit 340 uses the offset frequency distribution and the N raw images $I_n$ to separate water signals from fat signals (step S1004) so as to obtain water images and fat images. Note that the process in step S1004 will be referred to as a separation process.

The display processing unit 360 displays the water images and the fat images (collectively referred to as separated images) resulting from the separation on the display device 110 (step S1005).

<Pulse Sequence>

Figure 5:
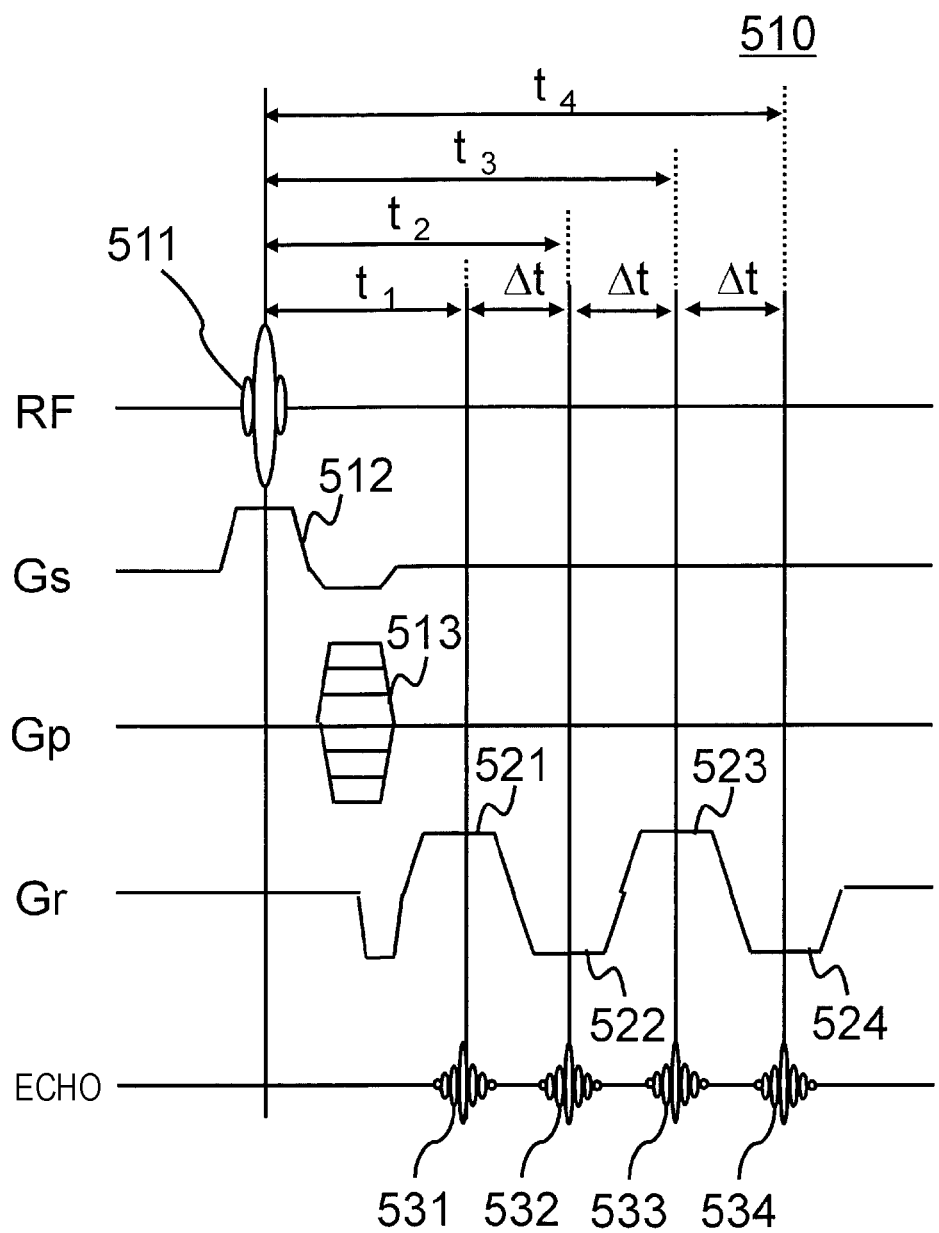
FIG. 5 is an explanatory diagram for explaining an example of a gradient echo pulse sequence according to the first embodiment.

Here, an example of the measurement sequence performed in the measurement in step S1001 by the measurement control unit 310 will be described. FIG. 5 illustrates an example of a time chart of the measurement sequence performed in the present embodiment. The measurement sequence 510 is a gradient echo (GrE) pulse sequence. In the measurement sequence 510, RF, Gs, Gp, and Gr represent application timings of an RF pulse, a slice selection gradient magnetic field, a phase encoding gradient magnetic field, and a readout gradient magnetic field, respectively. In addition, echo represents a timing for acquisition of an echo signal. The same applies to time charts in the present specifications below.

In the measurement sequence 510, echo signals are measured through the following procedures within one repetition time TR. Here, an example in which echo signals are acquired at four different echo times will be presented. A first echo time is represented by $t_1$, and intervals (echo intervals) between the subsequent echo times are $\Delta t$.

First, a RF pulse 511 is emitted to excite hydrogen nuclear spins of the subject 101. In this process, a slice selection gradient magnetic field (Gs) 512 is applied at the same time as the RF pulse 511 so as to select a specific slice of the subject 101. Subsequently, a phase encoding gradient magnetic field (Gp) 513 for phase encoding is applied to the echo signal. Thereafter, at time $t_1$ after first emission of the RF pulse 511, a readout gradient magnetic field (Gr) 521 is applied to measure the echo signal (first echo signal) 531. Furthermore, at time $t_2$ that is time $\Delta t$ from the measurement of the first echo signal 531, a readout gradient magnetic field (Gr) 522 with reversed polarity is applied to measure the echo signal (second echo signal) 532. Similarly, at time $t_3$ that is time $\Delta t$ from the measurement of the second echo signal 532, a readout gradient magnetic field (Gr) 523 with reversed polarity is applied to measure the echo signal (third echo signal) 533. Furthermore, at time $t_4$ that is time $\Delta t$ from the measurement of the third echo signal 533, a readout gradient magnetic field (Gr) 524 with reversed polarity is applied to measure the echo signal (fourth echo signal) 534.

The echo time $t_1$ and the echo intervals $\Delta t$ are set so that at least one of the echo times $t_1$, $t_2$, $t_3$, and $t_4$ at which the first echo signal 531, the second echo signal 532, the third echo signal 533, and the fourth echo signal 534 are measured is such a time that a phase difference between water and fat will not be 0. When a frequency difference between water and fat is represented by $f_{wf}$ and the time when water and fat become the same phase is represented by $t_{In}$, $t_{In}$ equals $m/f_{wf}$. Note that m is an integer.

In the measurement sequence 510, echo times $t_1$, $t_2$, $t_3$, and $t_4$ or an echo time $t_1$ and echo intervals $\Delta t$ that satisfy the above condition are selected. In the present embodiment, the echo times, the echo intervals, and the number of echo acquisitions are set by the user through the input device 115. Alternatively, these are set in advance.

The measurement control unit 310 repeats the measurement sequence 510, that is, emission of the RF pulse 511 to the predetermined imaged region of the subject 101 and measurements of the echo signals 531, 532, 533, and 534 from the region a predetermined number of times while changing the strength of the phase encoding gradient magnetic field 513. The number of repetitions is 128 or 256, for example. In this manner, acquisition of the echo signals is repeated, the number of echo signals being a number required for image reconstruction of the imaged region. One raw image (first raw image) is formed by the first echo signals 531, the number of first echo signals 531 being the number of repetitions, and a second raw image, a third raw image, and a fourth raw image are formed by the second echo signals 532, the third echo signals 533, and the fourth echo signals 534, respectively, the numbers of second echo signals 532, third echo signals 533, and fourth echo signals 534 being the number of repetitions. These are saved as raw images for calculating water images and fat images, which will be described later, in the storage device or the like.

Figure 6:
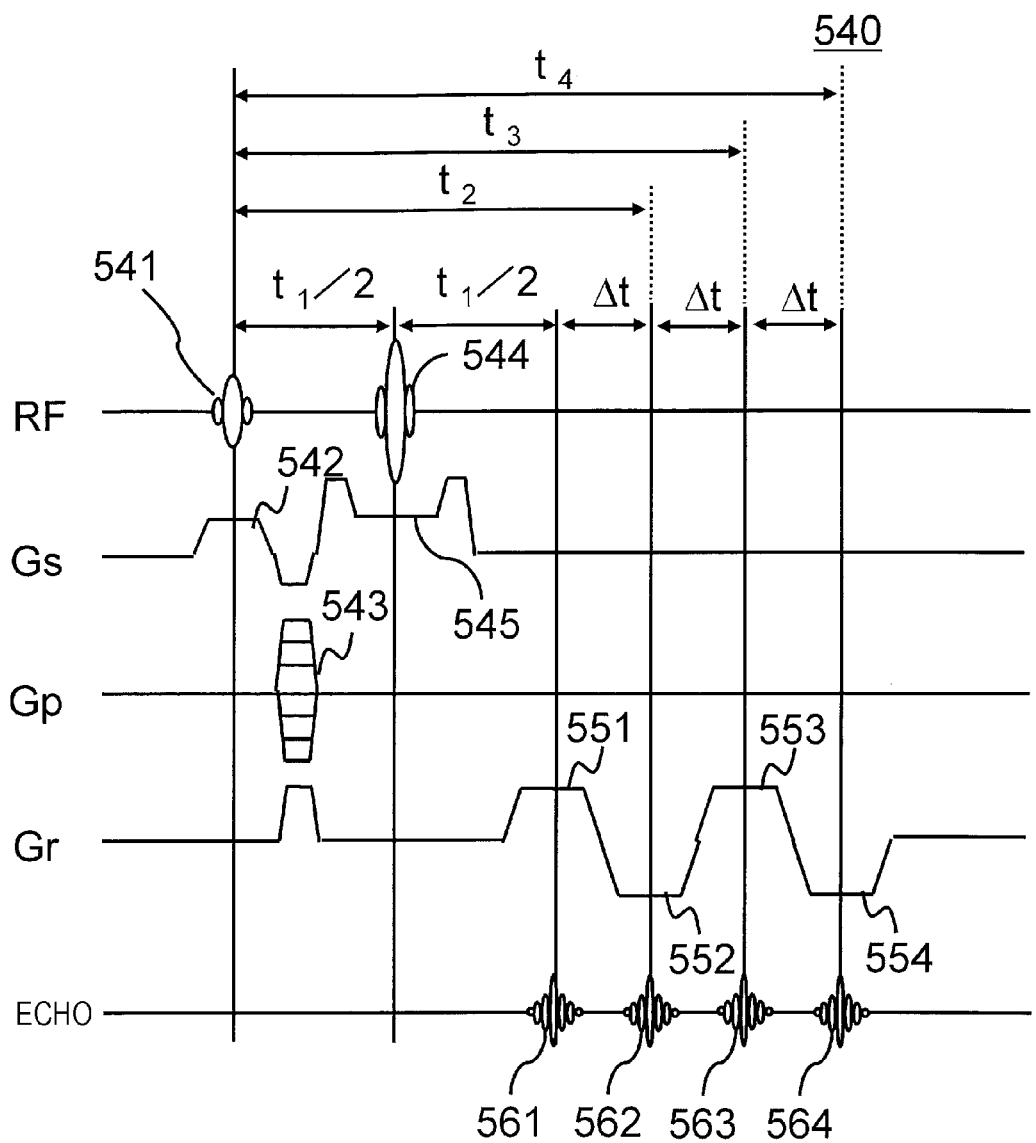
FIG. 6 is an explanatory diagram for explaining an example of a spin echo pulse sequence according to the first embodiment.

FIG. 6 illustrates another example of a time chart of the measurement sequence performed in the present embodiment. The measurement sequence 540 is a spin echo (SE) pulse sequence.

In the measurement sequence 540, echo signals are measure through the following procedures within one repetition time. Here as well, an example in which echo signals are acquired at four different echo times will be presented. In addition, a first echo time is represented by $t_1$ and subsequent echo intervals are time $\Delta t$.

First, a RF pulse 541 is emitted to excite hydrogen nuclear spins of the subject 101. In this process, a slice selection gradient magnetic field (Gs) 542 is applied at the same time as the RF pulse 541 so as to select a specific slice of the subject 101. Subsequently, a phase encoding gradient magnetic field (Gp) 543 for phase encoding is applied to the echo signal, and a RF pulse 544 for spin inversion is further emitted together with a slice selection gradient magnetic field (Gs) 545. Thereafter, at time $t_1$ after first emission of the RF pulse 541, a readout gradient magnetic field (Gr) 551 is applied to measure the echo signal (first echo signal) 561. Furthermore, at time $t_2$ that is time $\Delta t$ from the measurement of the first echo signal 561, a readout gradient magnetic field (Gr) 552 with reversed polarity is applied to measure the echo signal (second echo signal) 562. Similarly, at time $t_3$ that is time $\Delta t$ from the measurement of the second echo signal 562, a readout gradient magnetic field (Gr) 553 with reversed polarity is applied to measure the echo signal (third echo signal) 563. Furthermore, at time $t_4$ that is time $\Delta t$ from the measurement of the third echo signal 563, a readout gradient magnetic field (Gr) 554 with reversed polarity is applied to measure the echo signal (fourth echo signal) 564.

The echo times $t_1$, $t_2$, $t_3$, and $t_4$ at which the first echo signal 561, the second echo signal 562, the third echo signal 563, and the fourth echo signal 564 are measured are selected so that the same condition as that for the gradient pulse sequence will be satisfied.

In the examples illustrated in FIGS. 5 and 6, both in the GrE pulse sequence 510 and the SE pulse sequence 540, N signals (herein, a first echo signal, a second echo signal, a third echo signal, and a fourth echo signal) with different echo times are measured within one repetition time TR. Alternatively, however, one echo signal may be measured within one repetition time TR. In this case, four repetition times TR are used to measure a first echo signal, a second echo signal, a third echo signal, and a fourth echo signal.

Note that, in the examples of FIGS. 5 and 6, the reconstruction unit 320 places the echo signals at the respective echo times $t_1$, $t_2$, $t_3$, and $t_4$ measured in step S1001 in the k space and applies Fourier transform thereto in step S1002 described above. In this manner, a raw image $I_1$ (first raw image), a raw image $I_2$ (second raw image), a raw image $I_3$ (third raw image), and a raw image $I_4$ (fourth raw image) at the respective echo times $t_1$, $t_2$, $t_3$, and $t_4$ are calculated.

<Offset Frequency Distribution Calculation Process>

Next, a process of calculating the offset frequency distribution performed by the offset frequency distribution calculation unit 330 in step S1003 described above will be described. The offset frequency distribution calculation unit 330 of the present embodiment calculates each of a first peak frequency distribution that is a distribution of peak frequencies obtained on the assumption that all the pixels are of the first substance and a second peak frequency distribution that is a distribution of peak frequencies obtained on the assumption that all the pixels are of the second substance from raw images $I_n$ at N echo times, and uses the first peak frequency distribution and the second peak frequency distribution to obtain an offset frequency distribution in which aliasing (folding) due to the echo intervals is removed.

To achieve the above, the offset frequency distribution calculation unit 330 of the present embodiment uses, as illustrated in FIG. 3, includes a seed point extraction unit 331 that uses the raw images $I_n$ at the respective echo times to extract a seed point from pixels where the substance to be imaged (first substance, which is water herein) is the main component, a spectrum calculation unit 332 that uses the raw images $I_n$ at the respective echo times to calculate a spectrum of each pixel of the image of the imaged region, a peak frequency distribution calculation unit 333 that calculates peak frequencies of spectra of the pixels as a peak frequency distribution, a shifted frequency distribution calculation unit 334 that shifts the peak frequencies of the respective pixels for each of the first substance (water herein) and the second substance (fat herein) by predetermined shift amounts, and calculates a first shifted frequency (hereinafter referred to as a water shifted frequency) and a second shifted frequency (hereinafter referred to as a fat shifted frequency) for each of the pixels, and a peak frequency selection unit 335 that selects either of the peak frequency and the shifted peak frequency as an offset frequency for each of the pixels by a region expansion method using the seed point as a reference pixel to obtain an offset frequency distribution, in which the shift amounts are determined so that folding caused by the intervals of the echo times will be removed.

Figure 7:
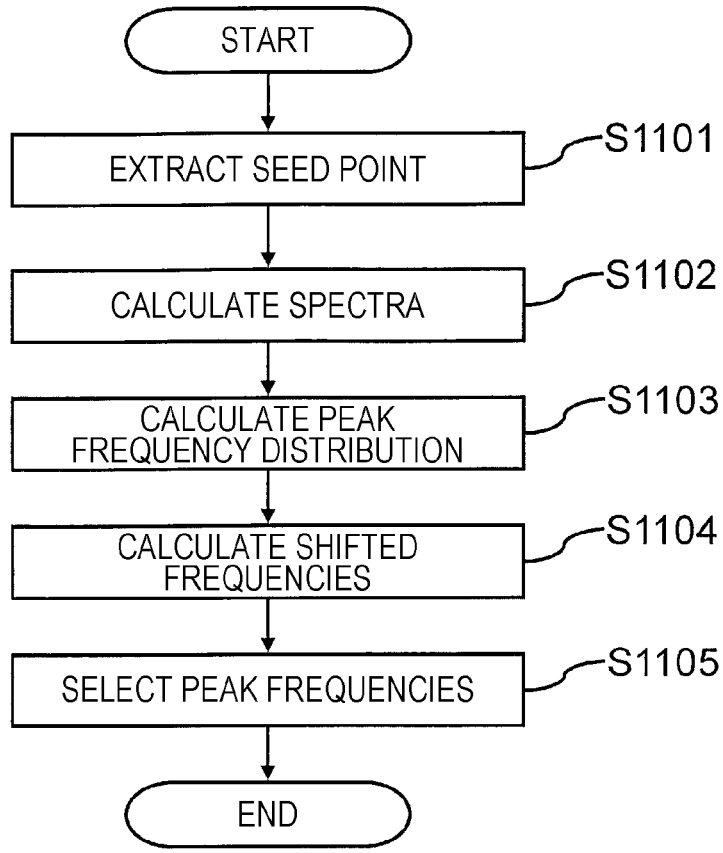
FIG. 7 is a flowchart of an offset frequency distribution calculation process according to the first embodiment.

First, an outline of a processing flow of the offset frequency distribution calculation process according to the present embodiment performed by the functions of the offset frequency distribution calculation unit 330 will be described. FIG. 7 is a flowchart for explaining the processing flow of the offset frequency distribution calculation process according to the present embodiment.

The seed point extraction unit 331 performs the seed point extraction process by using the raw images $I_n$ at the N echo times, and extracts one pixel among the pixels where water is the main component as a seed point (step S1101). Subsequently, the spectrum calculation unit 332 performs a spectrum calculation process of applying discrete Fourier transform to the signals at the N echo times in the time direction to calculate a spectrum of each of the pixels of the image of the imaged region (step S1102). Subsequently, the peak frequency distribution calculation unit 333 performs a peak frequency distribution calculation process to calculate a frequency (peak frequency) with the greatest amplitude in the spectrum of each of the pixels as peak frequency distribution (step S1103). Subsequently, the shifted frequency distribution calculation unit 334 performs a frequency shift process for each of the first substance and the second substance to calculate a shifted frequency distribution obtained by shifting frequency values that are pixel values of the peak frequency distribution by a predetermined shift amount (step S1104). The peak frequency selection unit 335 then performs a peak frequency selection process of selecting a pixel value of either of the shifted frequency distribution of the first substance and the shifted frequency distribution of the second substance for each of the pixels by the region expansion method using the seed point obtained in step S1101 (step S1105).

In the offset frequency distribution calculation process, either of the process of extracting the seed point in step S1101 and the process of calculating a spectrum of each of the pixels in step S1102 may be performed first. Details of the processes will be described below.

<Seed Point Extraction Process>

First, the seed point extraction process performed by the seed point extraction unit 331 in step S1101 will be described. The seed point extraction unit 331 extracts one pixel from pixels where water is the main component as a seed point to be used in the region expansion method, which will be described later. The seed point extraction unit 331 determines a pixel with a high SNR and a low signal decay with the apparent transverse relaxation rate $R_{2*}$ to be a pixel where water is the main component. A seed point is then extracted from pixels where water is the main component and with surrounding pixels where water is the main component.

In the water-fat separation method of the present embodiment, if a pixel where fat is the main component is selected as a seed point, a water image and a fat image that are finally obtained will be replaced with each other in the calculation. It is therefore necessary to extract a pixel where water is the main component as a seed point with high accuracy.

Figure 8:
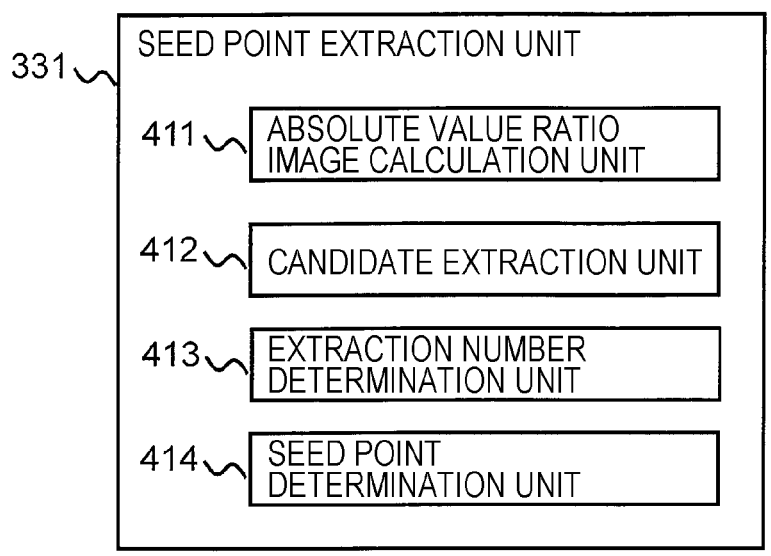
FIG. 8 is a functional block diagram of a seed point extraction unit according to the first embodiment.

To extract such a pixel as described above as a seed point, the seed point extraction unit 331 of the present embodiment includes, as illustrated in FIG. 8, an absolute value ratio image calculation unit 411 that calculates a ratio image and an absolute value thereof by using the raw images $I_n$ at the N echo times, a candidate extraction unit 412 that extracts a group of pixels that are seed point candidates from the absolute value ratio image, an extraction number determination unit 413 that determines whether or not a predetermined number or more seed point candidate pixels are extracted, and a seed point determination unit 414 that determines a seed point from the extracted seed point candidate pixels.

Figure 9:
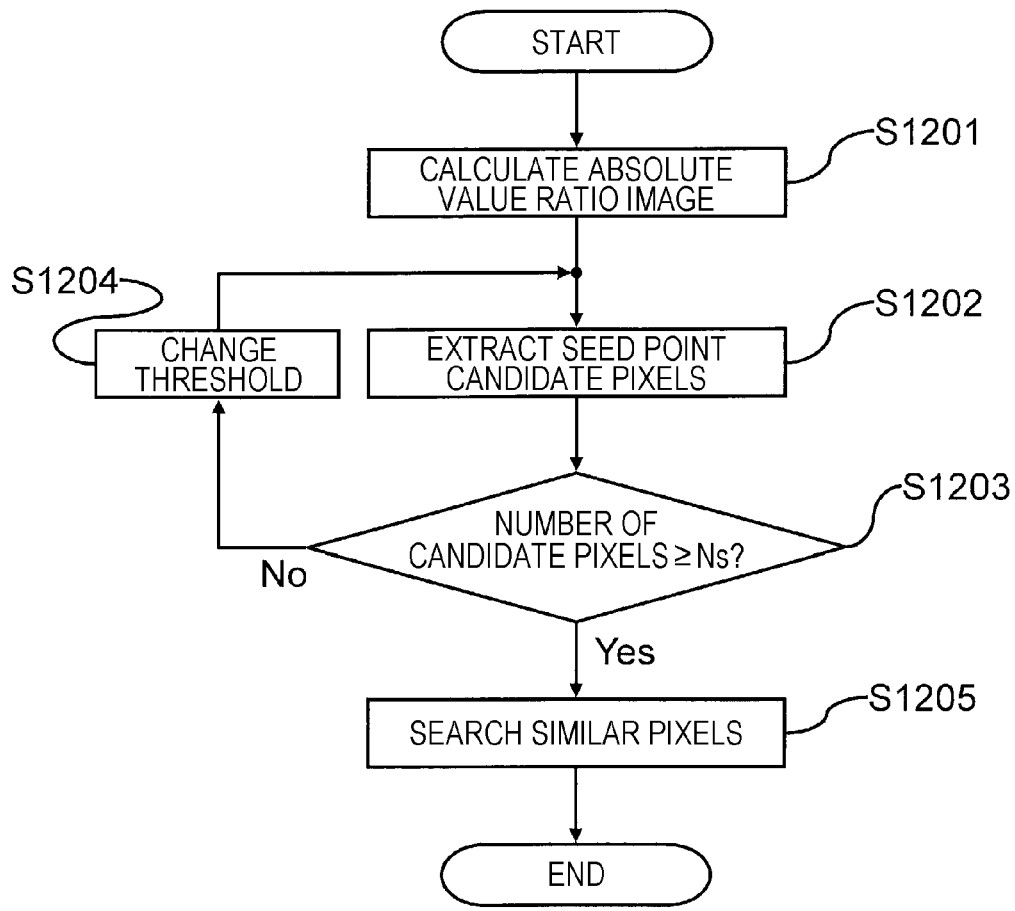
FIG. 9 is a flowchart of a seed point extraction process according to the first embodiment.

Here, a processing flow of the seed point extraction process performed by the respective components of the seed point extraction unit 331 and details of the respective components will be described. FIG. 9 is a flowchart for explaining the processing flow of the seed point extraction process of the present embodiment.

First, the absolute value ratio image calculation unit 411 calculates complex division of a signal value (pixel value) $s_n(r)$ of the n-th raw image $I_n$ with the signal value (pixel value) $s_1(r)$ of the first raw image $I_1$ for each of the pixels r, and obtains an absolute value signal ratio $u_n(r)$ that is an absolute value thereof (absolute value ratio image calculation; step S1201) according to the following expression (1):

$$u_n(r)=|s_n(r)/s_1(r)| \qquad (1).$$

In this process, the raw image used for the division is not limited to the first raw image. Any of the raw images may be used.

Subsequently, the candidate extraction unit 412 extracts a group of pixels (seed point candidate pixels) where water is the main component. Typically, a water signal is lower in temporal decay than a fat signal. In addition, a water signal has a higher SNR than a fat signal. In contrast, a fat signal is larger in signal decay with the apparent transverse magnetization relaxation rate ($R_{2*}$) than a water signal. Thus, an average of pixel values in the time direction of pixels where water is the main component is a value close to 1, while an average of pixel values in the time direction of pixels where fat is the main component is a value different from 1. Furthermore, when the SNR is high and the signal decay with $R_{2*}$ is small as in the case of water, a standard deviation of the pixel values is a value close to 0.

The candidate extraction unit 412 of the present embodiment makes use of the above property to extract a group of pixels where water is the main component as seed point candidate pixels. Specifically, the candidate extraction unit 412 calculates an average E(r) in the time direction and a standard deviation σ(r) of the absolute value signal ratios $u_n(r)$. The candidate extraction unit 412 then uses $Th_E$ and $Th_σ$ as predetermined thresholds for the average and the standard deviation, respectively, and extracts a group of pixels that satisfy $E(r) \geq Th_E$ and $σ(r) \leq Th_σ$ as the seed point candidate pixels (step S1202).

Note that empirically determined values are used for the thresholds $Th_E$ and $Th_σ$. Thus, when these thresholds are used, there may be cases where no seed point candidate pixel is extracted depending on the imaged region. To avoid this, the extraction number determination unit 413 determines whether or not one or more pixels are extracted as the seed point candidate pixels in step S1202 described above (step S1203). Specifically, the extraction number determination unit 413 determines whether or not the number of seed point candidate pixels is a predetermined reference number Ns (1 herein) for determination or larger.

Note that the extracted pixels may include a special pixel that is inappropriate as a seed point in subsequent processes. While the reference number Ns for determination is 1 above, it is therefore preferable that the reference number Ns for determination is 2 or larger.

When it is determined that no seed point candidate pixels are extracted, the seed point extraction unit 331 changes the threshold $Th_E$ to a smaller value by a predetermined change width and the threshold $Th_σ$ to a larger value by a predetermined change width (step S1204), returns to step S1202, and extracts seed point candidate pixels. Note that both of the thresholds may be changed or either one of the thresholds may be changed.

If it is determined in step S1203 that seed point candidate pixels are extracted, the seed point determination unit 414 conducts a similar pixel search (step S1205) to determine one pixel from the seed point candidate pixel group as the seed point.

Note that the pixel determined to be the seed point is preferably a pixel with the surrounding pixels also being pixels where water is the main component. The seed point determination unit 414 thus searches whether or not pixels where water is the main component are present around each of the seed point candidate pixels (similar pixel search), evaluates the search result according to predetermined criteria, and determines a pixel that is a seed point (seed point pixel) on the basis of the evaluation. Herein, among pixels r extracted as the seed point candidate pixels, a pixel r with a small area therearound including the most pixels where water is the main component is determined to be the seed point.

When pixels in a surrounding area of a seed point candidate pixel includes many pixels where water is the main component, an average within the area of the averages E(r) in the time direction of the pixels in the area is close to 1 and the standard deviation is close to 0. The seed point determination unit 414 makes use of this property and calculates, for each of one or more extracted seed point candidate pixels r, an average $E_a(r)$ within a small area of R×R pixels around the pixel r of the averages E(r) of the pixels in the area and a standard deviation $σ_a(r)$ of the averages E(r). The seed point determination unit 414 then uses a function h(r) expressed by the expression (2) below as an evaluation function and calculates an evaluation value that is a value of the evaluation function. The seed point determination unit 414 extracts a pixel with the greatest evaluation value of the seed point candidate pixels r as the seed point.

$$h(r)=E_a(r)/σ_a(r) \quad (2).$$

The seed point extraction unit 331 can extract a seed point with a high SNR and a low signal decay through the procedures described above. The seed point is used as a seed point in the region expansion method, which will be described later.

<Spectrum Calculation Process>

Next, the spectrum calculation process performed by the spectrum calculation unit 332 in step S1102 will be described. As described above, the spectrum calculation unit 332 applies a discrete Fourier transform, to the signals at the N echo times in the time direction to calculate a spectrum of each of the pixels of the image of the imaged region. The pixel values of the pixel in each raw image $I_n$ are used as the signals at the N echo times.

The spectrum calculation unit 332 first applies a discrete Fourier transform defined by the following expression (3) to a measurement signal $s_n(r)$ in the time domain for each pixel to calculate a spectral signal $S_f(r)$ in the frequency domain for each of the pixels r in the imaged region:

[Expression 3]

$$S_f(r) = \frac{1}{M} \sum_{m=-M/2}^{M/2-1} s_n(r) e^{-i2\pi m \Delta f_n} \quad (3)$$

In the expression, M and Δf represent a given number of frequency points and frequency resolution, respectively.

When the echo intervals of the N echo times of measurement are represented by Δt and a spectral range of a spectral signal $S_f(r)$ is represented by $B_w$, the spectral range $B_w$, the echo intervals Δt, the frequency resolution Δf, and the number of frequency points M satisfy the relation of the following expression (4):

$$B_w=(1/\Delta t)=M \cdot \Delta f \quad (4).$$

<Peak Frequency Distribution Calculation Process>

Next, the peak frequency distribution calculation process performed by the peak frequency distribution calculation unit 333 in step S1103 will be described. As described above, the peak frequency distribution calculation unit 333 obtains a peak frequency $\Psi_{peak}(r)$ of each pixel r, where aliasing is removed, from the calculated spectral signal $S_f(r)$ of each pixel.

First, the peak frequency distribution calculation unit 333 calculates the peak frequency $\Psi_{peak}(r)$ of the spectral signal $S_f(r)$ of each pixel r. The calculated peak frequency $\Psi_{peak}(r)$ may be calculated with a signal exceeding the spectral range $B_w$ is folded because of aliasing due to inhomogeneous magnetostatic field. Thus, the seed point extracted by the seed point extraction unit 331 is used to perform a frequency unwrapping process by the region expansion method to remove the folding.

Specifically, the pixel of the seed point is represented by $r_s$, and the peak frequency $\Psi_{peak}(r_s)$ of the seed point $r_s$ and a predetermined threshold $Th_{peak}$ are used to calculate a peak frequency $\Psi_{peak}(r_j)$ of a pixel $r_j$ adjacent to the seed point $r_s$ is calculated according to the following expression (5):

[Expression 5]

$$\psi_{peak}(r_j) = \begin{cases} \psi_{peak}(r_j), & \text{if } |\psi_{peak}(r_j) - \psi_{peak}(r_s)| \leq Th_{peak} \\ \psi_{peak}(r_j) - B_w, & \text{if } \psi_{peak}(r_j) - \psi_{peak}(r_s) > Th_{peak} \\ \psi_{peak}(r_j) + B_w, & \text{if } \psi_{peak}(r_j) - \psi_{peak}(r_s) < -Th_{peak} \end{cases} \quad (5)$$

Specifically, if an absolute value of a difference between the peak frequency $\Psi_{peak}(r_s)$ of the seed point $r_s$ and the peak frequency $\Psi_{peak}(r_j)$ of the adjacent pixel $r_j$ is within the threshold $Th_{peak}$, the value of the peak frequency $\Psi_{peak}(r_j)$ is used without any change as the peak frequency $\Psi_{peak}(r_j)$ of the adjacent pixel $r_j$, if the difference is larger than the threshold $Th_{peak}$, a value obtained by subtracting the spectral range $B_w$ is used, and if the difference is smaller than an inverse (additive inverse) of the threshold $Th_{peak}$, a value obtained by adding the spectral range $B_w$ is used.

The peak frequency distribution calculation unit 333 then resets the pixel $r_j$ to be a pixel $r_s$ of a new seed point, and calculates the peak frequency of an adjacent pixel by the aforementioned expression (5). This unwrapping process is repeated for all the pixels in the image, and the peak frequencies $\Psi_{peak}(r)$ of the respective pixels resulting from the unwrapping process are obtained as the peak frequency distribution.

Note that the threshold $Th_{peak}$ used in the unwrapping process is set to ½ of the spectral range $B_w$, for example. Alternatively, the threshold $Th_{peak}$ may have a variable value with an initial value of 0 and gradually increasing up to ½ of the maximum spectral range $B_w$. For example, the value of the threshold $Th_{peak}$ may be increased with the distance from the initially set seed point.

<Shifted Frequency Distribution Calculation Process>

Next, a frequency shift process performed by the shifted frequency distribution calculation unit 334 in step S1104 will be described. In the frequency shift process, a shifted frequency distribution obtained by shifting all the pixel values (peak frequencies) of the peak frequency distribution by a predetermined shift amount is calculated for each substance. The shift of the peak frequencies is achieved by subtracting a predetermined frequency (shift amount) from the peak frequencies of the respective pixels.

The shift amount is determined for each substance. Thus, in the present embodiment, the shifted frequency distributions of the respective substances calculated through the frequency shift process include a water shifted frequency distribution where all the pixels are assumed to be pixels where water is the main component and a fat shifted frequency where all the pixels are assumed to be pixels where fat is the main component.

The shift amount is calculated on the basis of the frequency difference between each substance and a reference substance. The reference substance is a substance for which parameters are set so that the peak frequency of a pixel where the substance is the main component becomes 0 in the absence of an inhomogeneous magnetostatic field. In the present embodiment, an example in which water is set to be the reference substance and the shift amount $F_{wf}$ is 0 for a pixel $r_w$ where water is the main component will be described.

Thus, when all the pixels are assumed to be pixels $r_w$ where water is the main component, the calculated peak frequencies $\Psi_{peak}(r)$ are the water shifted frequencies $\Psi_{shift\_w}(r)$ without any change. Specifically, a water shifted frequency $\Psi_{shift\_w}(r)$ when all the pixels are assumed to be pixels $r_w$ where water is the main component is expressed by the following expression (6) using the calculated peak frequency $\Psi_{peak}(r)$:

$$\Psi_{shift\_w}(r) = \Psi_{peak}(r) \quad (6).$$

For pixels $r_f$ where fat is the main component, the shift amount $F_{wf}$ is basically the frequency difference $f_{wf}$ (<0) between water and fat. If, however, the echo intervals $\Delta t$ do not satisfy the sampling theorem, the peak frequencies of fat are folded because of aliasing. Thus, for the pixels $r_f$ where fat is the main component, the shift amount $F_{wf}$ needs to be determined in view of the folding depending on the echo intervals $\Delta t$.

Here, when the absolute value $|f_{wf}|$ of the resonance frequency difference between water and fat is defined as a Nyquist frequency, and if a sampling frequency that is an inverse of the echo intervals (sampling intervals) is smaller than ½ of the Nyquist frequency, the sampling theorem is not satisfied. In other words, echo intervals that do not satisfy the sampling theorem are echo intervals $\Delta t$ larger than $1/(2 \times |f_{wf}|)$. Since the echo intervals $\Delta t$ and the spectral range $B_w$ satisfy the relation expressed by the expression (4), this corresponds to the case where the absolute value $|f_{wf}|$ of the resonance frequency difference between water and fat is larger than ½ of the spectral range $B_w$.

The fat shifted frequency $\Psi_{shift\_f}(r)$ when all the pixels are assumed to be pixels $r_f$ where fat is the main component is thus expressed by the following expression (7):

$$\Psi_{shift\_f}(r) = \Psi_{peak}(r) - F_{wf} \quad (7).$$

Here, the shift amount when the echo intervals $\Delta t$ satisfy the sampling theorem is assumed to be a resonance frequency difference $f_{wf}$ as expressed by the expression (8) below. When the sampling theorem is not satisfied, the spectral range $B_w$ is added to the resonance frequency difference $f_{wf}$ as expressed by the following expression (9) in view of folding because of aliasing so that the folding is removed.

$$F_{wf} = f_{wf}, \text{ if } |f_{wf}| \leq B_w/2 \quad (8),$$

$$F_{wf} = B_w + f_{wf}, \text{ if } |f_{wf}| > B_w/2 \quad (9).$$

In the offset frequency distribution calculation process, when the first substance is water and the second substance is fat as in the present embodiment, the shifted frequency distribution calculation unit may calculate the shifted frequency distribution only for the fat, and the peak frequency selection unit may select either of the peak frequency distribution and the shifted frequency distribution for each of the pixels to obtain the offset frequency distribution.

<Peak Frequency Selection>

Next, the peak frequency selection process performed by the peak frequency selection unit 335 will be described. In the peak frequency selection process, the calculated seed point is used for selecting either of the water shifted frequency and the fat shifted frequency as an offset frequency for each of the pixels by the region expansion method, and the offset frequency distribution is calculated.

Since the pixel of the seed point is a pixel where water is the main component, the peak frequency selection unit 335 first selects the water shifted frequency as the offset frequency for the pixel of the seed point. For an adjacent pixel, the peak frequency selection unit 335 then selects one of the water shifted frequency and the fat shifted frequency with a smaller difference from the offset frequency of the seed point as the offset frequency of the adjacent pixel. The peak frequency selection unit 335 then sets the adjacent pixel for which the offset frequency is selected to be a seed point, and repeats the same process until offset frequencies for all the pixels are selected.

Specifically, when the pixel of the seed point is represented by $r_s$, $\Psi_{off}(r_s)=\Psi_{shift\_w}(r_s)=\Psi_{peak}(r_s)$ is first set. An offset frequency $\Psi_{off}(r_j)$ of a pixel $r_j$ adjacent to the pixel $r_s$ is then calculated by the aforementioned expressions (6) and (7) according to the following expression (10):

[Expression 10]

$$\psi_{off}(r_j) = \begin{cases} \psi_{peak}(r_j), & \text{if } |\psi_{peak}(r_j) - \psi_{off}(r_s)| \leq \\ & |(\psi_{peak}(r_j) - F_{wf}) - \psi_{off}(r_s)| \\ \psi_{peak}(r_j) - F_{wf}, & \text{if } |\psi_{peak}(r_j) - \psi_{off}(r_s)| > \\ & |(\psi_{peak}(r_j) - F_{wf}) - \psi_{off}(r_s)| \end{cases} \quad (10)$$

The pixel $r_j$ is then reset to be the pixel $r_s$ of a new seed point, and the process of calculating the offset frequency $\Psi_{off}(r_j)$ of the pixel $r_j$ by the expression (10) is repeated until the offset frequencies for all the pixels in the image are calculated, and an offset frequency distribution $\Psi_{off}(r)$ is calculated.

<Separation Process>

Next, the separation process performed by the separation unit 340 in step S1004 will be described. The separation unit 340 of the present embodiment first sets a signal model indicating variations in signal strengths of water and fat with the echo times, and various initial values for a fitting process, which will be described later. The raw images $I_n$ at N different echo times, the initial values, and the signal model are then used for calculation of water images and fat images by the non-linear least-squares method.

Figure 10:
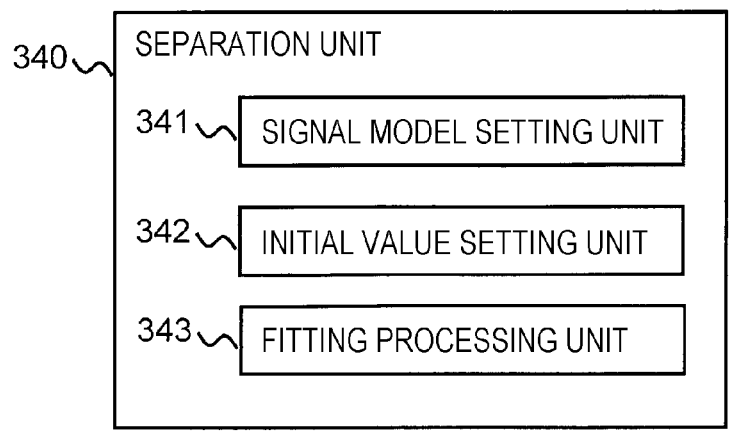
FIG. 10 is a functional block diagram of a separation unit according to the first embodiment.

To achieve the above, the separation unit 340 of the present embodiment includes, as illustrated in FIG. 10, a signal model setting unit 341 that sets a signal model indicating variations in signal strengths of water and fat with the echo times, an initial value setting unit 342 that sets various initial values to be used for the fitting process, which will be described later, and a fitting processing unit 343 that fits the raw images $I_n$ (measurement signals acquired through actual measurement) at the N different echo times to the signal model by the non-linear least-squares method by using the set initial values to separate water and fat from each other.

Figure 11:
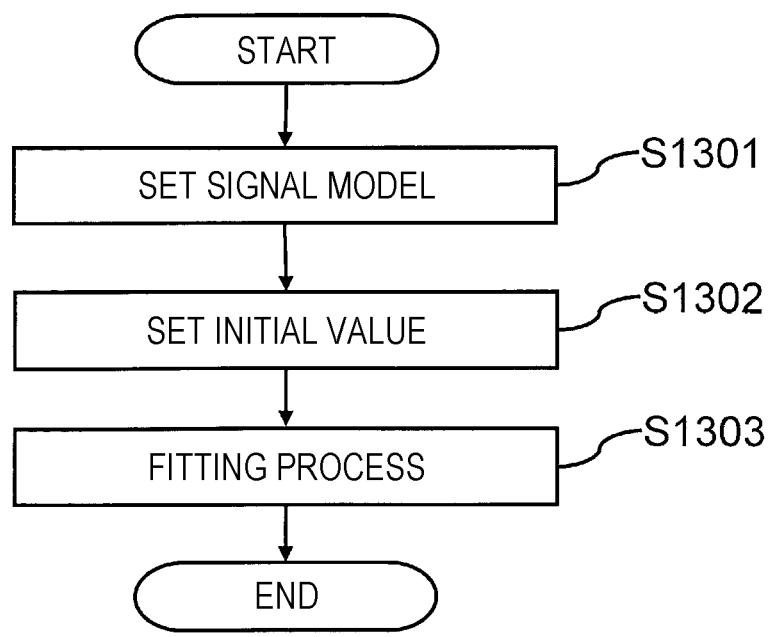
FIG. 11 is a flowchart of a separation process according to the first embodiment.

A processing flow of the separation process performed by the respective components of the separation unit 340 of the present embodiment will be described with reference to FIG. 11. First, the signal model setting unit 341 sets the aforementioned signal model (step S1301). Subsequently, the initial value setting unit 342 sets the aforementioned initial values (step S1302). The fitting processing unit 343 then performs the fitting process of fitting the measurement signals to the signal model by the non-linear least-squares method by using the initial values (step S1303) to separate water and fat from each other. Details of the processes will be described below.

<Signal Model Setting>

First, the signal mode setting performed by the signal model setting unit 341 in step S1301 will be described. In the present embodiment, a signal model having the signal strength of water, the signal strength of fat, the offset frequency, the apparent relaxation rate $R_{2*}$ as fitting variables is set. Here, a signal model $s'_n$ indicating the signal strength $s_n$ (n=1, . . . , N) at a given pixel of an image $I_n$ reconstructed from an echo signal acquired at the n-th echo time $t_n$ is expressed by the expression (11):

[Expression 11]

$$s'_n = (\rho_w + K_n \rho_f) e^{-R_2^* t_n} e^{i2\pi\Psi t_n} \quad (11)$$

In the expression, $t_n$ represents the n-th echo time, $\Psi$ represents the offset frequency caused due to an inhomogeneous magnetostatic field, $\rho_w$ and $\rho_f$ represent complex signal strengths of water and fat, respectively, $K_n$ represents a phase change amount (complex number) of a fat signal at time $t_n$, and $R_{2*}$ represents an apparent transverse magnetization relaxation rate that is common to water and fat.

In calculations below, a signal decay term in the expression (11) of the signal model $s'_n$ is subjected to Taylor expansion approximation as expressed in the following expression (12) for simplicity:

[Expression 12]

$$s'_n \approx (\rho_w + K_n \rho_f)(1 - R_2^* t_n) e^{i2\pi\Psi t_n} \quad (12)$$

Note that a fat signal is known to have a plurality of spectral peak due to the molecular structure thereof. When a fat signal having P (P is an integer of 1 or larger) is assumed, the phase change amount $K_n$ of the fat signal is expressed by the following expression (13):

[Expression 13]

$$K_n = \sum_{p=1}^{P} a_p e^{-i2\pi f_p t_n} \quad (13)$$

where $a_p$ and $f_p$ represent a relative signal strength and a frequency difference from water, respectively, of the p-th (p is an integer satisfying 1≤p≤P) fat peak. Note that $a_p$ satisfies the condition of the following expression (14):

[Expression 14]

$$\sum_{p=1}^{P} a_p = 1 \quad (14)$$

Hereinafter, in the present embodiment, a signal model $s'_n$ expressed by the expression (12) in which fat has six peaks (P=6) will be used.

<Initial Value Setting>

Next, a method for setting initial values by the initial value setting unit 342 in step S1302 will be described. The initial values to be set are the complex signal strength of water and the complex signal strength of fat of each of the pixels, the offset frequency distribution, and the apparent transverse magnetization relaxation rate $R_{2*}$.

For the initial values of the complex signal strength $\rho_w$ of water and the complex signal strength $\rho_f$ of fat of each of the pixels, a value $|s_n|_{max}$ obtained by maximum intensity projection in the time direction of an absolute value $|s_n|$ of a signal value $s_n$ of a raw image acquired by actual measurement is used. For the initial value of the offset frequency distribution, the offset frequency distribution $\Psi_{off}(r)$ calculated by the offset frequency distribution calculation unit 330; and the initial value of the apparent transverse magnetization relaxation rate $R_{2*}$ is 1 for all of the pixels.

Note that the initial values of the complex signal strengths $\rho_w$ and $\rho_f$ of water and fat of each of the pixels and the initial value of the apparent transverse magnetization relaxation rate $R_{2*}$ need not necessarily be the values mentioned above, and may be any values that do not make results of calculation by the non-linear least-squares method diverge or fluctuate.

<Fitting Process>

Next, the fitting process performed by the fitting processing unit 343 in step S1303 will be described. In the present embodiment, variables whose true values are to be estimated by fitting are the signal strength of water represented by $\rho_w$, the signal strength of fat represented by $\rho_f$, the apparent transverse magnetization relaxation rate represented by $R_{2*}$, and the offset frequency represented by $\Psi$ for each of the pixels. Estimation values of the respective variables are represented by $\rho_w'$, $\rho_f'$, $R_{2*}'$, and $\Psi'$, and differences between the true values and the estimation values are represented by $\Delta\rho_w$, $\Delta\rho_f$, $\Delta R_{2*}$, and $\Delta\Psi$, respectively.

In this process, when the signal value acquired by actual measurement is represented by $s_n$ and an estimation signal obtained by substituting the estimation values $\rho_w'$, $\rho_f'$, $R_{2*}'$, and $\Psi'$ into the signal model expressed by the expression (12) is represented by $s'_n$, the difference $\Delta s_n$ between the measurement signal $s_n$ and the estimation signal $s'_n$ is expressed by a matrix notation by the following expression (15):

[Expression 15]

$$\Delta s = Ax \quad (15)$$

where $$\Delta s = \begin{bmatrix} \Delta s_1 \\ \vdots \\ \Delta s_N \end{bmatrix}, x = \begin{bmatrix} \Delta\rho_w \\ \Delta\rho_f \\ \Delta\psi \\ \Delta R_2^* \end{bmatrix}, A = \begin{bmatrix} \frac{\partial s'_1}{\partial \rho_w} & \frac{\partial s'_1}{\partial \rho_f} & \frac{\partial s'_1}{\partial \psi} & \frac{\partial s'_1}{\partial R_2^*} \\ \vdots & \vdots & \vdots & \vdots \\ \frac{\partial s'_N}{\partial \rho_w} & \frac{\partial s'_N}{\partial \rho_f} & \frac{\partial s'_N}{\partial \psi} & \frac{\partial s'_N}{\partial R_2^*} \end{bmatrix}$$

A vector x can therefore be calculated by the following expression (16) using a pseudo inverse matrix of the matrix A:

[Expression 16]

$$x = (A^H A)^{-1} A^H \Delta s \quad (16)$$

where $A_H$ represents a complex conjugate transpose of A.

The fitting processing unit 343 adds $\Delta\rho_w$, $\Delta\rho_f$, $\Delta R_{2*}$, and $\Delta\Psi$ that are elements of the difference vector x calculated by the expression (16) to the estimation values $\rho_w'$, $\rho_f'$, $R_{2*}'$, and $\Psi'$, respectively, to recalculate an estimation signal $s'_n$, and then recalculate the difference vector x by using the expression (16).

These procedures are repeated to minimize the difference vector x and make the estimation values closer to the true values. The fitting processing unit 343 sets a given threshold and repeats the above-described procedures until the difference vector x becomes the threshold or smaller. The signal strength $\rho_w'$ of water and the signal strength $\rho_f'$ of fat of each of the pixels which are finally obtained are assumed to be a water image and a fat image, and the water image and the fat image are separated from each other.

While an example in which water is the substance to be imaged, fat is the unnecessary substance, and the water image and the fat image are separated from each other so that signals from the unnecessary substance (fat) are suppressed in the finally obtained image has been described in the present embodiment, the substances to be separated are not limited thereto. Any two substances with a frequency difference therebetween that is a chemical shift being a predetermined value or larger may be separated.

As described above, the computer 109 of the MRI apparatus 100 of the present embodiment includes the measurement control unit 310 that measures the nuclear magnetic resonance signals from the imaged region at three or more different echo times according to a predetermined imaging sequence, the reconstruction unit 320 that reconstructs a raw image of the imaged area at each of the three or more different echo times from each of the nuclear magnetic resonance signals at the echo times, the offset frequency distribution calculation unit 330 that calculates the offset frequency distribution that is a distribution of offset frequencies within the imaged region from the raw images at the respective echo times, and the separation unit 340 that uses the raw images at the respective echo times and the offset frequency, distribution to separate signals of the first substance from signals of the second substance, and obtain an image of the first substance and an image of the second substance of the imaged region, in which the first substance and the second substance are different in resonance frequency, the offset frequency is an offset component of a resonance frequency that varies owing to an inhomogeneous magnetostatic field, the offset frequency distribution calculation unit 330 includes the seed point extraction unit 331 that uses the raw images at the respective echo times to extract a seed point from pixels where the first substance is the main component, the spectrum calculation unit 332 that uses the raw images at the respective echo times to calculate a spectrum of each pixel of the image of the imaged region, the peak frequency distribution calculation unit 333 that calculates peak frequencies of spectra of the pixels as a peak frequency distribution, the shifted frequency distribution calculation unit 334 that shifts the peak frequencies of the respective pixels for each of the first substance and the second substance by predetermined shift amounts, and calculates a first shifted frequency and a second shifted frequency for each of the pixels, and the peak frequency selection unit 335 that selects either of the first shifted frequency and the second shifted frequency for each of the pixels by a region expansion method using the seed point as a reference pixel to obtain the offset frequency distribution, in which the shift amounts are determined so that folding caused by the intervals of the echo times will be removed.

In this manner, according to the present embodiment, in the Dixon's method in which measurement is perform at three or more different echo times, the offset frequency distribution is calculated so that folding caused by the echo time intervals will be removed. The offset frequencies of the respective pixels are selected from shifted frequencies obtained by shifting the peak frequencies for each of the substances so that folding will be removed. The shift amounts are basically calculated on the basis of the resonance frequency difference between substances to be separated, but the spectral bandwidth is further added thereto if the echo times do not satisfy the sampling theorem.

As a result, according to the present embodiment, even when the echo intervals do not satisfy the sampling theorem, folding of the peak frequencies can be removed during the processing. A highly accurate peak frequency distribution for each substance can therefore be obtained regardless of the echo intervals. Furthermore, since the highly accurate peak frequency distribution is used to obtain an offset frequency distribution, a highly accurate offset frequency distribution can be obtained.

Thus, according to the present embodiment, even when the echo intervals do not satisfy the sampling theorem, the offset frequency distribution can be used to obtain highly accurately separated images of the first substance and the second substance without being replaced with each other. In the Dixon's method, there is therefore no restriction on the setting of echo intervals, and the echo acquisition times can be set so that desired resolution and signal-to-noise ratio will be satisfied.

According to the present embodiment, restriction on echo intervals can therefore be reduced in the Dixon's method without sacrificing separation performance and image quality.

Furthermore, since the unwrapping process is performed in calculation of the peak frequency distribution, the peak frequencies that are bases of the offset frequency distribution calculation can be calculated with high accuracy. Separation can therefore be finally performed with high accuracy.

Furthermore, since a seed point used for performing the region expansion method in the unwrapping process and the peak frequency selection process for calculating a peak frequency distribution is selected with high accuracy from pixels where the first substance to be imaged is the main component, the peak frequency distribution and the offset frequency distribution can be obtained with high accuracy. Images can therefore be finally separated with high accuracy.

Second Embodiment

Next, a second embodiment of the present invention will be described. In the first embodiment, the number of echoes, the echo times, and the echo intervals for acquiring images at different echo times are set in advance. In contrast, in the present embodiment, only the number of echoes is set, and the echo intervals are automatically calculated wo that the SNR will be highest depending on the set number of echoes.

A MRI apparatus 100 used in the present embodiment basically has the same configuration as that in the first embodiment. Hereinafter, the present embodiment will be described focusing on a configuration different from that in the first embodiment. In the present embodiment, similarly to the first embodiment, an example in which the first substance is water and the second substance is fat will be described.

Figure 12:
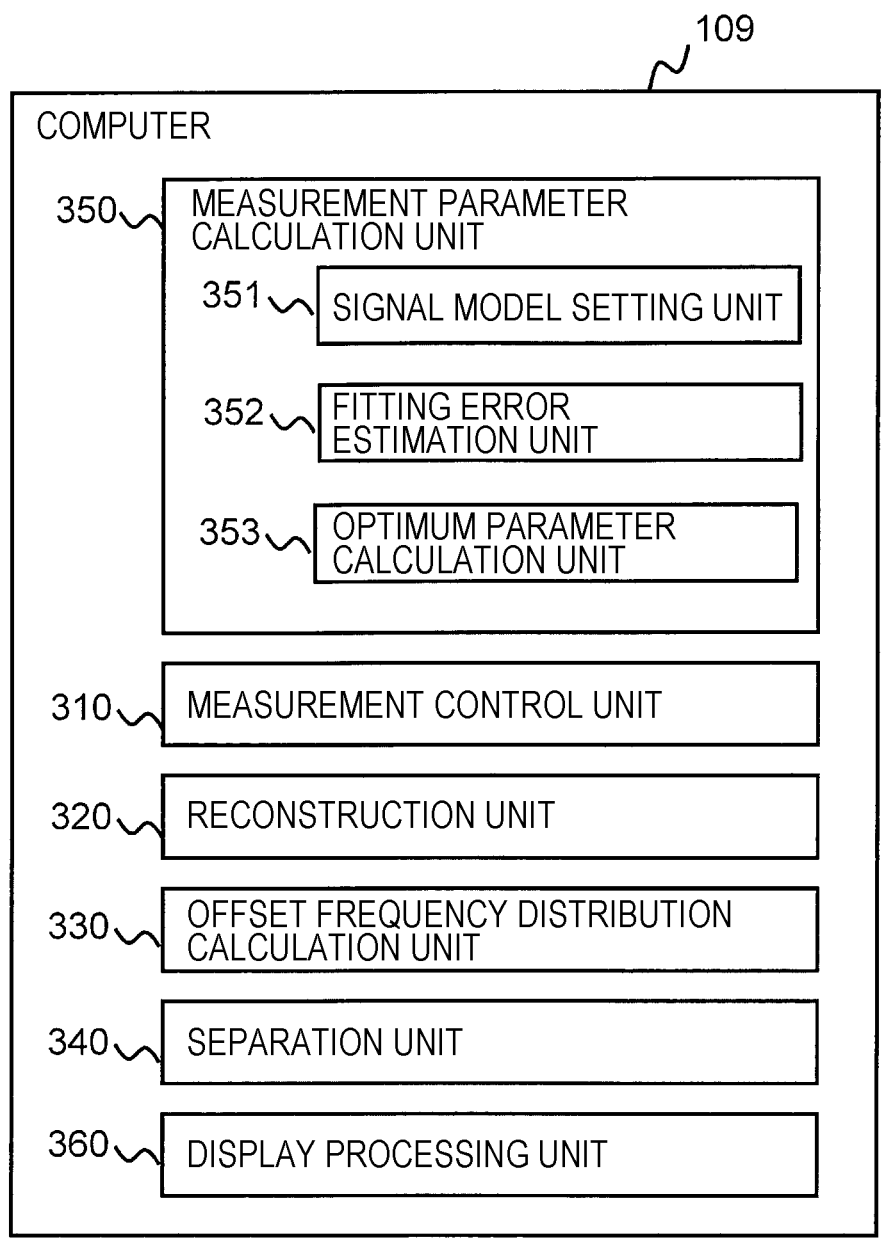
FIG. 12 is a functional block diagram of a computer according to the second embodiment.

As illustrated in FIG. 12, a computer 109 of the present embodiment has basically the same configuration as that of the first embodiment. In the present embodiment, however, when the number N of echoes is set by the user, for example, as described above, echo intervals with which the SNR will be highest is calculated. Thus, a measurement parameter calculation unit 350 that calculates optimum echo intervals Δt depending on the predetermined number N of acquisition echoes is further included. A measurement control unit 310 of the present embodiment uses the optimum echo intervals Δt calculated by the measurement parameter calculation unit 350 to perform measurement similarly to the first embodiment. Hereinafter, details of the measurement parameter calculation unit 350 of the present embodiment will be described.

<Measurement Parameter Calculation Unit>

The measurement parameter calculation unit 350 of the present embodiment first sets a signal model indicating signal strengths of water and fat that vary with the echo times. This signal model is used for assumption of a standard deviation of noise contaminated during measurement. Errors in a water image and a fat image resulting from fitting are estimated from the standard deviation, and echo intervals that minimizes the fitting errors to maximize the SNR are calculated as optimum measurement parameters.

<Functional Configuration>

To achieve the above, the measurement parameter calculation unit 350 of the present embodiment includes, as illustrated in FIG. 12, a signal model setting unit 351 that sets a signal model indicating variations in signals strengths of water and fat with the echo times, a fitting error estimation unit 352 that assumes as standard deviation of noise contaminated during measurement, and estimates errors in a water image and a fat image resulting from fitting from the standard deviation, and an optimum parameter calculation unit 353 that calculates echo intervals that minimizes the fitting errors to maximize the SNR.

<Processing Flow>

Figure 13:
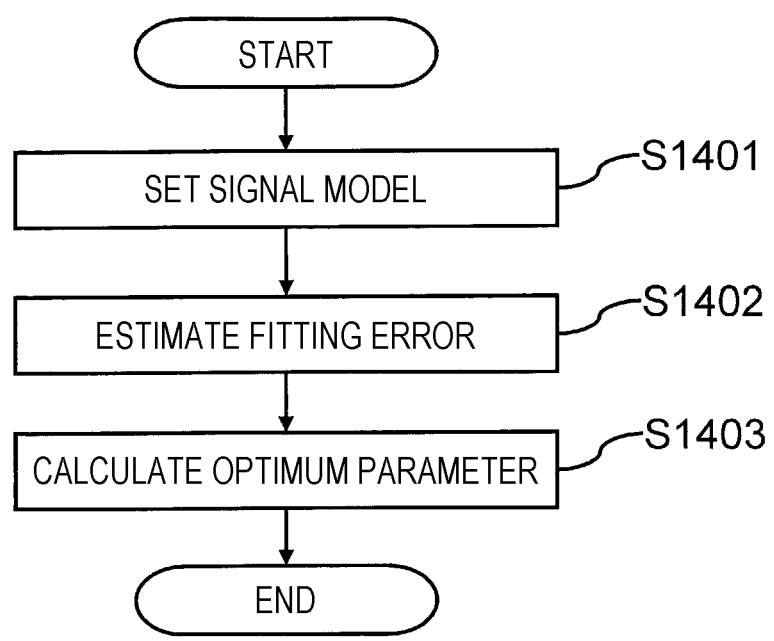
FIG. 13 is a flowchart of a measurement parameter calculation process according to the second embodiment.

An outline of a processing flow of a measurement parameter calculation process performed by the measurement parameter calculation unit 350 of the present embodiment with the functions described above will be described. FIG. 13 is a flowchart for explaining the processing flow of the measurement parameter calculation process of the present embodiment.

The signal model setting unit 351 sets a signal model indicating signal strengths of water and fat that vary with the echo times (step S1401). Subsequently, the fitting error estimation unit 352 assumes a standard deviation of noise contaminated during measurement, and estimates errors in a water image and a fat image resulting from fitting from the standard deviation (step S1402). The optimum parameter calculation unit 353 then calculates an optimum value of a measurement parameter (optimum parameter) that minimizes the fitting errors to maximize the SNR (step S1403). In the present embodiment, the measurement parameter whose optimum value is calculated is the echo intervals Δt. Details of the processes will be described below.

<Signal Model Setting Process>

First, the signal model setting performed by the signal model setting unit 351 in step S1401 will be described. The signal model setting unit 351 of the present embodiment ignores the terms of the offset frequency Ψ and the apparent transverse magnetization relaxation rate $R_{2*}$ and sets a signal model s' where only the signal strength of water and the signal strength of fat are fitting variables. Here, a signal model $s'_n$ of a signal $s_n$ at the n-th echo time (n=1, ..., N) in a certain pixel set by the signal model setting unit 351 is expressed by the following expression (17):

$$s'_n = \rho_w + K_n \rho_f \tag{17}$$

In the expression, $\rho_w$ and $\rho_f$ represent complex signal strengths of water and fat, and $K_n$ represents a phase change amount (complex number) of a fat signal at time $t_n$. Note that $t_n$ represents the n-th echo time. Furthermore, in the present embodiment, a single peak model is used for a fat signal. In this case, the phase change amount $K_n$ of a fat signal is expressed by the following expression (18) where the frequency difference between water and fat is represented by $f_{wf}$.

[Expression 18]

$$K_n = e^{-i2\pi f_{wf} t_n} \quad (18)$$

<Fitting Error Estimation>

Next, a fitting error estimation method performed by the fitting error estimation unit 352 in step S1402 will be described. In the present embodiment, an error propagation method is used to calculate the influence of noise contaminated during measurement on the fitting results is calculated. Hereinafter, a processing flow thereof will be described.

First, as illustrated in the following expression (19), a differential coefficient matrix B for the signal model $s'_n$ is defined, and a pseudo inverse matrix L thereof is calculated:

[Expression 19]

$$L = (B^H B)^{-1} B^H \quad (19)$$

where $$L = \begin{bmatrix} L_{11} & \cdots & L_{1N} \\ L_{21} & \cdots & L_{2N} \end{bmatrix}, B = \begin{bmatrix} \frac{\partial s'_1}{\partial \rho_w} & \frac{\partial s'_1}{\partial \rho_f} \\ \vdots & \vdots \\ \frac{\partial s'_N}{\partial \rho_w} & \frac{\partial s'_N}{\partial \rho_f} \end{bmatrix}$$

and where $B_H$ represents a complex conjugate transpose of the differential coefficient matrix B.

Here, when the standard deviation of noise contained in the signal $s_n$ measured at the n-th echo time $t_n$ is represented by $\sigma_0$, and the standard deviations of the estimated water signal strength and fat signal strength are represented by $\sigma_w$ and $\sigma_f$, respectively, the relation of the following expression (20) is satisfied:

[Expression 20]

$$\sigma_w^2 = \left[ \sum_{n=1}^{N} (L_{1n})^2 \right] \sigma_0^2$$

$$\sigma_f^2 = \left[ \sum_{n=1}^{N} (L_{2n})^2 \right] \sigma_0^2 \quad (20)$$

<Optimum Parameter Calculation>

Next, an optimum parameter calculation method performed by the optimum parameter calculation unit 353 in step S1403 will be described.

First, the optimum parameter calculation unit 353 uses the estimated errors (standard deviations) to calculate effective cumulative numbers $NSA_w$ and $NSA_f$ for the number N of echoes in the water image and the fat image calculated by the least squares approximation. The effective cumulative numbers $NSA_w$ and $NSA_f$ are respectively expressed by the following expression (21):

[Expression 21]

$$NSA_w = \frac{\sigma_0^2}{\sigma_w^2} = \frac{1}{\sum_{n=1}^{N} (L_{1n})^2}$$

$$NSA_f = \frac{\sigma_0^2}{\sigma_f^2} = \frac{1}{\sum_{n=1}^{N} (L_{2n})^2} \quad (21)$$

Note that the effective cumulative numbers $NSA_w$ and $NSA_f$ calculated by the expression (21) have a minimum value of 0 and a maximum value within the range of the number N of echoes.

To search for optimum echo intervals Δt for the number N of echoes, an evaluation function G(N, Δt) expressed by the following expression (22) is defined:

[Expression 22]

$$G(N, \Delta t) = \frac{NSA_w(N, \Delta t) + NSA_f(N, \Delta t)}{2} \quad (22)$$

The optimum parameter calculation unit 353 of the present embodiment uses the expression (22) to calculate the echo intervals Δt with which the evaluation function G is the maximum for the number N of echoes.

Through these procedures, the measurement parameter calculation unit 350 calculates the echo intervals Δt with which the SNR is maximum for the number N of echoes as an optimum measurement parameter.

Alternatively, the measurement parameter calculation unit 350 may present the optimum measurement parameter (echo intervals Δt) calculated through the above-described procedures to the user via the display device 110.

The measurement control unit 310 of the present embodiment performs measurement similarly to the first embodiment by using the optimum measurement parameter calculated by the measurement parameter calculation unit 350. The reconstruction unit 320 reconstructs a raw image at each of the echo times from a measurement result in the same manner as in the first embodiment. The offset frequency distribution calculation unit 330 calculates the offset frequency in the same manner as in the first embodiment, and the separation unit 340 separates a water image and a fat image from each other in the same manner as in the first embodiment.

As described above, the MRI apparatus 100 of the present embodiment further includes the measurement parameter calculation unit that calculates optimum echo intervals depending on the number of echo times at which nuclear magnetic resonance signals are measured, in addition to the configuration in the first embodiment.

According to the present embodiment, the measurement parameter calculation unit calculates echo intervals that maximize the SNR, and performs measurement by using the echo intervals. Thus, in addition to the effects produced by the first embodiment, an image with a higher SNR than that in the first embodiment can be obtained. Since this is used to separate a water image and a fat image from each other, both images can be separated with high accuracy. In other words, according to the present embodiment, an image in which signals from an unnecessary substance are suppressed with high accuracy can be obtained with reduced restriction on the echo intervals.

While a signal model where the terms of the offset frequency Ψ and the apparent transverse magnetization relaxation rate $R_{2*}$ are ignored is used in the present embodiment, a signal model where these are taken into account may alternatively be used. Furthermore, while a single peak model is used for a fat model, a multi-peak model may alternatively be used. In calculation of an optimum parameter, a value optimizing the initial echo time (reference echo time) $t_1$ may also be calculated in addition to the echo intervals $\Delta t$.

When the terms of the offset frequency Ψ and the apparent transverse magnetization relaxation rate $R_{2*}$ are considered, the expression (11) or (12) is used instead of the expression (17), for example. When a multi-peak model is used, the expression (13) is used instead of the expression (18), for example. Furthermore, when $t_1$ is also optimized, a three-dimensional evaluation function G'(N, $\Delta t$, $t_1$) to which $t_1$ is added is defined instead of the evaluation function G(N, $\Delta t$) of the expression (22), for example, and the echo intervals $\Delta t$ and the echo time $t_1$ with which the evaluation function is maximized are calculated. The measurement parameter calculation unit 350 determines the obtained echo intervals $\Delta t$ and echo time $t_1$ to be the optimum measurement parameter that maximizes the SNR for the number N of echoes.

REFERENCE SIGNS LIST

100 MRI apparatus
101 subject
102 static magnetic field coil
103 gradient coil
104 shim coil
105 transmitter coil
106 receiver coil
107 transmitter
108 receiver
109 computer
110 display device
111 external storage device
112 gradient magnetic field power supply unit
113 shim power supply unit
114 sequence controller
115 input device
120 MRI apparatus
130 MRI apparatus
310 measurement control unit
320 reconstruction unit
330 offset frequency distribution calculation unit
331 seed point extraction unit
332 spectrum calculation unit
333 peak frequency distribution calculation unit
334 shifted frequency distribution calculation unit
335 peak frequency selection unit
340 separation unit
341 signal model setting unit
342 initial value setting unit
343 fitting processing unit
350 measurement parameter calculation unit
351 signal model setting unit
352 fitting error estimation unit
353 optimum parameter calculation unit
360 display processing unit
411 absolute value ratio image calculation unit
412 candidate extraction unit
413 extraction number determination unit
414 seed point determination unit
510 GrE pulse sequence
511 RF pulse
512 slice selection gradient magnetic field
513 phase encoding gradient magnetic field
521 readout gradient magnetic field
522 readout gradient magnetic field
523 readout gradient magnetic field
524 readout gradient magnetic field
531 first echo signal
532 second echo signal
533 third echo signal
534 fourth echo signal
540 SE pulse sequence
541 RF pulse
542 slice selection gradient magnetic field
543 phase encoding gradient magnetic field
544 RF pulse
545 slice selection gradient magnetic field
551 readout gradient magnetic field
552 readout gradient magnetic field
553 readout gradient magnetic field
554 readout gradient magnetic field
561 first echo signal
562 second echo signal
563 third echo signal
564 fourth echo signal

The invention claimed is:

1. A magnetic resonance imaging apparatus comprising:
a magnetostatic field generation part configured to generate a magnetostatic field in a space in which a subject is placed;
a transmitting unit configured to transmit a radio frequency magnetic field pulse to the subject;
a receiving unit configured to receive nuclear magnetic resonance signals generated from the subject as a result of irradiation with the radio frequency magnetic field pulse;
a gradient magnetic field application part configured to apply a gradient magnetic field to add positional information to the nuclear magnetic resonance signals; and
a computer configured to control operations of the transmitting unit, the receiving unit, and the gradient magnetic field application part to measure the nuclear magnetic resonance signals, and perform computation on the measured nuclear magnetic resonance signals to obtain an image of a predetermined region to be imaged, wherein
the computer includes:
a measurement control unit configured to measure the nuclear magnetic resonance signals of the imaged region at three or more different echo times according to a predetermined imaging sequence;
a reconstruction unit configured to reconstruct a raw image of the imaged region from at each of the three or more echo times from each of the nuclear magnetic resonance signals at the echo times;
an offset frequency distribution calculation unit configured to calculate an offset frequency distribution that is a distribution of offset frequencies in the imaged region from the raw images at the respective echo times; and
a separation unit configured to separate signals from a first substance and signals from a second substance from each other by using the raw images at the respective echo times and the offset frequency distribution to obtain an image of the first substance and an image of the second substance in the imaged region, the first substance and the second substance are different in resonance frequency, the offset frequency is an offset component of a resonance frequency that varies owing to an inhomogeneous magnetostatic field, the offset frequency distribution calculation unit includes:
- a seed point extraction unit configured to use the raw images at the respective echo times to extract a seed point from pixels where the first substance is the main component,
- a spectrum calculation unit configured to use the raw images at the respective echo times to calculate a spectrum of each pixel of the image of the imaged region,
- a peak frequency distribution calculation unit configured to calculate peak frequencies of spectra of the pixels as a peak frequency distribution,
- a shifted frequency distribution calculation unit configured to shift the peak frequencies of the respective pixels for each of the first substance and the second substance by predetermined shift amounts, and calculate a first shifted frequency and a second shifted frequency for each of the pixels, and
- a peak frequency selection unit configured to select either of the first shifted frequency and the second shifted frequency for each of the pixels by a region expansion method using the seed point as a reference pixel to obtain the offset frequency distribution, and the shift amounts are determined so that folding caused by the intervals of the echo times will be removed.

2. The magnetic resonance imaging apparatus according to claim 1, wherein the first substance is water and the second substance is fat.

3. The magnetic resonance imaging apparatus according to claim 2, wherein echo intervals that are intervals of adjacent echo times of the three or more different echo times are constant, the shift amount of the first substance is 0, and the shift amount of the second substance is determined by using the resonance frequency difference between the first substance and the second substance depending on the echo intervals.

4. The magnetic resonance imaging apparatus according to claim 3, wherein when the echo intervals do not meet a sampling theorem, the shift amount of the second substance is an amount obtained by adding a spectral range to the resonance frequency difference.

5. The magnetic resonance imaging apparatus according to claim 2, wherein the peak frequency distribution calculation unit obtains a peak frequency of a spectrum of each of the pixels, and performs an unwrapping process on the obtained peak frequency of each of the pixels by a region expansion method using the seed point as a reference pixel to calculate the peak frequency distribution.

6. The magnetic resonance imaging apparatus according to claim 2, wherein the peak frequency selection unit selects a shifted frequency with a smaller difference from an offset frequency of the reference pixel from the first shifted frequency and the second shifted frequency of a pixel adjacent to the reference pixel as an offset frequency of the adjacent pixel.

7. The magnetic resonance imaging apparatus according to claim 2, wherein the seed point extraction unit includes:
- an absolute value ratio image calculation unit configured to calculate an absolute value ratio image having absolute values of ratios of the pixels as pixels by using the raw images at the respective echo times,
- a candidate extraction unit configured to extract a group of pixels that are seed point candidates from an absolute value ratio image,
- an extraction number determination unit configured to determine whether or not a predetermined number of or more pixels of the seed point candidates are extracted, and
- a seed point determination unit configured to determine a seed point from the extracted pixels of the seed point candidates when the predetermined number of or more pixels of the seed point candidates are determined to be extracted, and the ratios of the pixels are obtained by dividing pixel values of a raw image that is a reference among the raw images at the respective echo times by a pixel value of another raw image.

8. The magnetic resonance imaging apparatus according to claim 7, wherein the candidate extraction unit calculates an average in a time direction and a standard deviation for each of the pixels of the absolute value ratio image, and extracts a pixel with the average in the time direction being a predetermined first threshold or larger and the standard deviation being a predetermined second threshold or lower as a pixel of a seed point candidate.

9. The magnetic resonance imaging apparatus according to claim 7, wherein the seed point determination unit determines a pixel of a seed point candidate with a predetermine area therearound including the most pixels where the first substance is a main component of the pixels of the seed point candidates to be the seed point.

10. The magnetic resonance imaging apparatus according to claim 9, wherein the seed point determination unit determines a pixel with a value obtained by dividing an average within the predetermined area of the averages in the time direction of the pixel values by the standard deviation within the predetermined area being the largest of the pixels of the seed point candidates to be the seed point.

11. The magnetic resonance imaging apparatus according to claim 2, wherein the separation unit includes:
- a signal model setting unit configured to set a signal model indicating variations in signal strengths of water and fat with echo times;
- an initial value setting unit configured to set initial values to be used in a fitting process; and
- a fitting processing unit configured to fit the raw images at the echo times to the signal model by using the initial values to obtain an image of the first substance and an image of the second substance.

12. The magnetic resonance imaging apparatus according to claim 1, wherein the computer further includes a measurement parameter calculation unit configured to calculate optimum echo intervals depending on the number of echo times at which the nuclear magnetic resonance signals are measured, and the measurement control unit measures the nuclear magnetic resonance signals with the optimum echo intervals according to a predetermined imaging sequence.

13. The magnetic resonance imaging apparatus according to claim 12, wherein the measurement parameter calculation unit includes:
- a signal model setting unit configured to set a signal model indicating variations in signal strengths of water and fat with echo times;
- a fitting error estimation unit configured to assume a standard deviation of noise contaminated during measurement, and estimate errors in a water image and a fat image resulting from fitting from the standard deviation; and an optimum parameter calculation unit configured to calculate the optimum echo intervals that minimizes fitting errors.

14. A magnetic resonance imaging apparatus comprising:
a magnetostatic field generation part configured to generate a magnetostatic field in a space in which a subject is placed;
a transmitting unit configured to transmit a radio frequency magnetic field pulse to the subject;
a receiving unit configured to receive nuclear magnetic resonance signals generated from the subject as a result of irradiation with the radio frequency magnetic field pulse;
a gradient magnetic field application part configured to apply a gradient magnetic field to add positional information to the nuclear magnetic resonance signals; and
a computer configured to control operations of the transmitting unit, the receiving unit, and the gradient magnetic field application part, and perform computation on the measured nuclear magnetic resonance signals, wherein
the computer includes:
  a measurement control unit configured to obtain the nuclear magnetic resonance signals at three or more different echo times according to a predetermined pulse sequence;
  a reconstruction unit configured to reconstruct a raw image from at each of the three or more echo times from each of the nuclear magnetic resonance signals at the echo times;
  an offset frequency distribution calculation unit configured to calculate an offset frequency distribution that is a distribution of offset components of resonant frequencies varying owing to an inhomogeneous magnetostatic field from the raw images at the respective echo times; and
  a separation unit configured to separate signals from a first substance and signals from a second substance from each other by using the raw images at the respective echo times and the offset frequency distribution,
the offset frequency distribution calculation unit calculates a first peak frequency distribution and a second peak frequency distribution in which folding due to the echo time intervals is removed from the raw images at the respective echo times, and obtains the offset frequency distribution by using the first peak frequency distribution and the second peak frequency distribution, and the first peak frequency distribution and the second peak frequency distribution are a distribution of peak frequencies obtained on an assumption that all of the pixels are the first substance and a distribution of peak frequencies obtained on an assumption that all of the pixels are the second substance, respectively.

15. A method for separating water and fat in an image acquired by a magnetic resonance imaging apparatus, the method comprising:
performing a measurement control process of measuring nuclear magnetic resonance signals of an imaged region at three or more different echo times according to a predetermined imaging sequence;
performing a reconstruction process of reconstructing a raw image of the imaged region from at each of the three or more echo times from each of the nuclear magnetic resonance signals at the echo times;
performing an offset frequency distribution calculation process of calculating an offset frequency distribution that is a distribution of offset frequencies in the imaged region from the raw images at the respective echo times; and
separating signals from water and fat from each other by using the raw images at the respective echo times and the offset frequency distribution to obtain a water image and a fat image in the imaged region, wherein
the offset frequency is an offset component of a resonance frequency that varies owing to an inhomogeneous magnetostatic field,
the offset frequency distribution calculation process includes:
  using the raw images at the respective echo times to extract a seed point from pixels where water is the main component,
  using the raw images at the respective echo times to calculate a spectrum of each pixel of the image of the imaged region,
  calculating a distribution of peak frequencies of spectra of the pixels,
  calculating a distribution of shifted frequencies by shifting the peak frequencies of the respective pixels according to a frequency difference between water and fat by predetermined shift amounts, and
  selecting either of the peak frequency and the shifted frequency for each of the pixels by a region expansion method using the seed point as a reference pixel to obtain the offset frequency distribution, and
the shift amounts are determined so that folding caused by the intervals of the echo times will be removed.

* * * * *